United States Patent
Stamets

(10) Patent No.: US 8,501,207 B2
(45) Date of Patent: *Aug. 6, 2013

(54) MYCOATTRACTANTS AND MYCOPESTICIDES

(76) Inventor: Paul Stamets, Shelton, WA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/066,566

(22) Filed: Apr. 18, 2011

(65) Prior Publication Data

US 2011/0200551 A1 Aug. 18, 2011

Related U.S. Application Data

(60) Division of application No. 12/288,535, filed on Oct. 20, 2008, now Pat. No. 7,951,389, which is a division of application No. 10/853,059, filed on May 24, 2004, now abandoned, which is a division of application No. 09/969,456, filed on Oct. 1, 2001, now Pat. No. 7,122,176, which is a continuation-in-part of application No. 09/678,141, filed on Oct. 4, 2000, now Pat. No. 6,660,290.

(51) Int. Cl.
*A01N 25/32* (2006.01)

(52) U.S. Cl.
USPC ............ 424/406; 424/84; 424/93.5; 424/405; 424/409; 424/411; 435/179; 435/254.1

(58) Field of Classification Search
None
See application file for complete search history.

(56) References Cited

PUBLICATIONS

Arcas—et al—J. of Biotechnology (1999) 67 (2,3), 151-158 Bioinsecticidal acitivity of conidia & Dry Mycelium.*

\* cited by examiner

*Primary Examiner* — Neil Levy
(74) *Attorney, Agent, or Firm* — William R. Hyde

(57) ABSTRACT

The present invention utilizes extracts of the pre-sporulation (preconidial) mycelial stage of entomopathogenic fungi as insect attractants and/or pathogens. The fungus can be cultivated on grain, wood, agricultural wastes or other cellulosic material. More than one fungus and substrate can be used in combination.

20 Claims, No Drawings

MYCOATTRACTANTS AND MYCOPESTICIDES

This application is a divisional of U.S. patent application Ser. No. 12/288,535, filed Oct. 20, 2008, which is a divisional of U.S. patent application Ser. No. 09/969,456, filed Oct. 1, 2001 (now issued as U.S. Pat. No. 7,122,176), which is a continuation-in-part of U.S. patent application Ser. No. 09/678,141, filed Oct. 4, 2000 (now issued as U.S. Pat. No. 6,660,290).

BACKGROUND OF THE INVENTION

1. Field of the Invention

The present invention relates to mycology, entomology and the use of fungal mycelium as insect attractants (mycoattractants) and biopesticides (mycopesticides). More particularly, the invention relates to the control and destruction of insects, including termites, fire ants, carpenter ants, flies, beetles, cockroaches, grasshoppers and other pests, using pre-sporulation fungal mycelium as an attractant and/or infectious agent.

2. Description of the Related Art

Insects are among the most diverse and numerous life forms on earth. While the majority of the one million named species of insects are considered beneficial, somewhere from 1% to 5% are considered to be pests. These insect pests cause tremendous losses in terms of direct destruction of crops, livestock and human dwellings and vector pathogens including protozoans, bacteria, viruses and *rickettsia* that cause devastating human health problems. The physical, mental, economic, social, and ecological implications of these pest insects are immeasurable on any scale.

The use of chemical pesticides is the cause of many secondary environmental problems aside from the death of the targeted pest. Numerous problems attributed to chemical pesticides are caused or compounded by widespread application necessitated by lack of suitable means of attracting the targeted pest to the pesticide. Communities are increasingly in need of natural solutions to pest problems.

Compounding these problems, many pest type or vermin insects have developed a broad spectrum of resistance to chemical pesticides, resulting in few commercially available pesticides that are effective without thorough and repeated applications. In addition to being largely ineffective and difficult and costly to apply as presently utilized, chemical pesticides present the further disadvantage of detrimental effects on non-target species, resulting in secondary pest outbreaks. Widespread use of broad-spectrum insecticides may destroy or greatly hamper the natural enemies of pest species, with pest species reinfesting the area faster than non-target species, thereby allowing and encouraging further pest outbreaks. Van Driesche, R. G. and T. S. Bellows Jr., *Biological Control*, Chapman & Hall, pp. 4-6 (1996). Further exacerbating these problems, introduced "alien" insect pests such as termites or fire ants often have few or no natural enemies. There is a particular need for natural alternatives.

Biological control agents have been tried with varying results. Bacteria such as *Bacillus thuringiensis* are used with some success as a spray on plants susceptible to infestation with certain insects. Fungal control agents are another promising group of insect pathogens suitable for use as biopesticides. However, limited availability, lack of effective delivery systems, reliability and cost has hampered the development of such fungal control agents. Host range and specificity has been a problem as well as an advantage: a fungal pathogen that is pathogenic (capable of causing disease) and virulent (in the sense of being extremely infectious, malignant or poisonous) to one insect species may be ineffective against other species, even closely related species of the same family or genus. However, some success has been demonstrated.

The typical lifecycle of the entomopathogenic (capable of causing insect disease) fungi is thought to involve adhesion of the spore(s) to the host insect cuticle, spore germination, penetration of the cuticle prior to growth in the hemocoel, death, saprophytic feeding, hyphal reemergence and sporulation. For example, U.S. Pat. No. 6,254,864 (2001) to Stimac et al. discloses dry powder *Beauveria bassiana* spore and spore/mycelium compositions for control of cockroaches and ants including carpenter ants, pharaoh ants and fire ants. U.S. Pat. No. 4,925,663 (1990) to Stimac discloses *Beauveria bassiana* used to control fire ants (*Solenopsis*). Rice, mycelia and spores (conidia) mixture may be applied to fire ants or used as a bait and carried down into the nest, thereby introducing spores. U.S. Pat. No. 5,683,689 (1997) to Stimac et al. discloses conidial control of cockroaches, carpenter ants, and pharaoh ants using strains of *Beauveria bassiana* grown on rice. U.S. Pat. No. 5,413,784 (1995) to Wright et al. discloses compositions and processes directed to the use of *Beauveria bassiana* and *Paecilomyces fumosoroseus* to control boll weevils, sweet potato whiteflies and cotton fleahoppers. U.S. Pat. No. 5,728,573 (1998) to Sugiura et al. discloses germinated fungi and rested spore termiticides of entomogenous fungus such as *Beauveria brongniartii, Beauveria bassiana, Beauveria amorpha, Metarhizium anisopliae* and *Verticillium lecanii* for use against insects such as termites, cockroaches, ants, pill wood lice, sow bugs, large centipedes, and shield centipedes. U.S. Pat. No. 5,939,065 (1999) and U.S. Pat. No. 6,261,553 (2001) to Bradley et al. discloses conidial formulations of *Beauveria* and methods for control of insects in the grasshopper family. U.S. Pat. No. 4,942,030 (1990) to Osborne discloses control of whiteflies and other pests with *Paecilomyces fumosoroseus* Apopka spore conidia formulations. The *Paecilomyces* fungus is also useful for control of *Diptera, Hymenoptera, Lepidoptera, Bemisia, Dialeurodes, Thrips, Spodoptera* (beet army worm), *Leptinotarsa* (Colorado potato beetle), *Lymantria* (Gypsy moth), *Tetranychus, Frankliniella, Echinothrips, Planococcus* (citrus mealybug) and *Phenaococcus* (solanum mealybug). U.S. Pat. No. 5,360,607 to Eyal et al. discloses prilled *Paecilomyces fumosoroseus* compositions utilizing mycelium grown via submerged fermentation to produce conidia to control various insects including whiteflies, mosquitoes, aphids, planthoppers, spittlebugs, mites, scales, thrips, beetles or caterpillars. U.S. Pat. No. 5,165,929 (1992) to Howell discloses use of *Rhizopus nigricans* and other fungus in the order Mucorales as a fungal ant killer. U.S. Pat. No. 5,989,898 (1999) to Jin et al. is directed to packaged fungal conidia, particularly *Metarhizium* and *Beauveria*. The scientific journal literature also discusses similar uses of conidial preparations.

One disadvantage to such approaches is that the fungal lifecycle may be particularly sensitive to and dependent upon conditions of humidity, moisture and free water, particularly during the stages of spore germination and sporulation after death of the insect.

A particular disadvantage with conidial preparations becomes apparent from U.S. Pat. No. 5,595,746 (1997) to Milner et al. for termite control, which discloses *Metarhizium anisopliae* conidia utilized as a termite repellant in uninfested areas and as a termite control method in infested areas. The difficulties of utilizing conidia or conidia/mycelium as a bait and/or contact insecticide are readily apparent when considering that conidia are effective as an insect repellant to termites and are repellant in varying degrees to most or all targeted insect pests. A repellant, of course, does not facilitate use as a bait or contact insecticide. This may be a factor in explaining why fungal insecticides have all too often proven more effective in the laboratory, where conidia may be unavoidable in the testing chamber or even directly applied to insects, than in the field.

U.S. Pat. No. 5,888,989 (1999) to Kern discloses synergistic combinations of conidia of entomopathogenic fungi such as *Beauveria* and *Metarhizium* with parapyrethroid insect compositions such as silafluofen and etofenprox, nitromethylenes such as imidacloprid, carbamates such as fenoxycarb and phenylpyrazoles such as fipronil. Problems remain with the repellency of the spores, the repellency of the pesticides and the use of conidia as a vector of infection.

Certain sexually reproducing brown-rot fungi (such as *Lenzites trabea*), dry rot fungi and other fungi are known to influence termite behaviors in laboratory and field tests, demonstrating attractant properties, eliciting trail-following, etc. See, for example, U.S. Pat. No. 4,363,798 (1982) to D'Orazio for termite baits utilizing brown rot fungus as an attractant mixed with toxicant boron compounds. The brown-rot fungus *Lentinus lepideus* and aqueous extracts of this fungus were found to be extremely lethal to termites in the laboratory, U.S. Pat. No. 3,249,492 (1966) to Lund. Certain fungi are known to produce substances that elicit trail-following in Rhinotermitidae in the laboratory, i.e., *Gloephyllum trabeum, Oligoporous balsameus* and *Serpula lacrimans*. Various extracts of the sexually reproducing Zygomycetes fungus *Micromucor ramannianus* and other fungi coexisting with *Reticulitermes* have also been shown to exhibit phagostimulatory (feeding stimulatory) effects and phagodeterrent effects. See U.S. Pat. No. 6,203,811 (2001) to McPherson et al. However, there remains a need for improved fungal attractants and pesticides.

The fresh, dried and rehydrated mycelium of entomopathogenic fungi has been utilized as a spore source in both the laboratory and field. See, for example, the U.S. patents above, where conidia are directly or indirectly produced from solid substrate or liquid fermentor grown mycelium. Pre-sporulation mycelium of *Metarhizium anisopliae, Metarhizium flaviride, Beauveria bassiana, Paecilomyces farinosus, Paecilomyces lilacinus* and *Hirsutella citriformis* has also been utilized as a spore source in agricultural fields for use against various subterranean and agricultural pests including the black vine weevil, the cranberry girdler (*Chrysoteuchia topiaria*), sod webworm, rice brown planthopper, stem borer, European corn borer and fall armyworm. See Booth and Shanks Jr., Potential of a Dried Rice/Mycelium Formulation of Entomopathogenic Fungi to Suppress Subterranean Pests in Small Fruits, *Biocontrol Science and Technology*, 8: pp. 197-206 (1998); Rombach et al., Infection of Rice Brown Planthopper, *Nilaparvata lugens* (Homoptera: Delphacidae), by Field Application of Entomopathogenic Hyphomycetes (Deuteromycotina), *Environmental Entomology*, 15(5): pp. 999-1110 (1986); and Maniania, Evaluation of three formulations of *Beauveria bassiana* (Bals.) Vuill. for control of the stem borer *Chilo partellus* (Swinhoe) (Lep., Pyralidae), *Journal of Applied Entomology*, 115: pp. 266-272 (1993). Pre-sporulation vegetative mycelium has also been a focus with the Entomophthorales mycopesticidal fungi such as *Zoophthora radicans*, which produce fragile, thin-walled spores that are difficult to mass produce, harvest and formulate on an industrial scale, thus leading to investigations of the also somewhat delicate and ephemeral mycelium. After being applied to the crop or soil, the mycelium produces spores that infect the target pests. See, for example, U.S. Pat. No. 4,530,834 (1985) to McCabe et al. Pre-sporulation mycelium of *Hirsutella citriformis* has been also been utilized in the field as conidia of the fungi are difficult to produce due to low sporulation rates, slime production of the mycelium and irregular growth patterns.

Another continuing problem with existing techniques for combating pests including social insects has been inconsistent bait acceptance. Baits are often bypassed and left uneaten by social insects such as termites and carpenter ants, which are hard to attract. Such may be a particular problem with insects such as termites and carpenter ants, as opposed to house ants and cockroaches, because it is usually not possible to remove competing food sources for termites and carpenter ants. Attractants, pheromones and feeding stimulants have sometimes increased the consistency of bait acceptance, but such increases cost and complexity, and there remains a continuing need for improved baits with improved bait acceptance.

There is, therefore, a continuing need for improved attractants and baits in general. There is a continuing need for enhancing the effectiveness of entomopathogenic fungal biopesticide products and methods and enhancing the attractiveness of such fungal pesticides to insects. There is also a need for improved packaging, shipping and delivery methods.

In view of the foregoing disadvantages inherent in the known types of insect control agents, the present invention provides improved fungal biocontrol agents and methods of using such agents.

SUMMARY OF THE INVENTION

The present invention offers an environmentally benign approach to insect control by attracting insects that contact or ingest "preconidial" mycelium of mycopesticidal/entomopathogenic fungi (that is, mycelium in a developmental state prior to conidia or spore formation). Such preconidial mycelium may be used solely as an attractant (either as an attractant for pest insects or as an attractant for beneficial insects) or as an attractant and pathogen where the preconidial mycelium is both the attractant and the pathogenic agent. Where attractant mycopesticidal strains are utilized with social insects, the infected insects carrying the fungal hyphae become a vector back to the central colony, further dispersing the mycopesticidal mycelium. The preconidial mycopesticidal mycelium can grow within an insect, can grow via spread to another insect or can grow via spread to an organic debris housing and subsequent insect infestation. Thus, multiple avenues of growth and infection are provided while entirely avoiding the supposed "necessity" of conidia germination as a means of infection.

The preconidial mycelium of mycopesticidal fungi is grown in pure culture using standard techniques for in vitro propagation. Once inoculated onto a substrate such as grain or wood, the mycelia matures to a state prior to conidia formation. The window of utility extends from post-spore germination through all stages of mycelial growth prior to sporulation. The preconidial mycelium may be utilized as is or may be arrested in its development through means such as flash chilling, freeze-drying, air-drying, refrigeration or gaseous cooling and packaged in spoilage-proof or sealed packages. The end-user facilitates opening the package and placing the exposed mycelia contents in the vicinity of recent pest activity. For use as an attractant, extracts of the preconidial mycelium may also be utilized. It is envisioned that the fungal attractants and/or pesticides may be used in conjunction with any type of appropriate trap or attractant disseminator or delivery system as is known to the art.

The present invention thus provides improved products and methods wherein the fungal mycelium acts as food and attractant and/or as an ingested or contact insecticide, palatable enough that insects will readily consume it even in the presence of competing food sources, with high recruitment of other insects among insects that exhibit such behavior. This results in multiple visits to a highly attractive (and potentially virulent) food, thereby providing numerous individual insect and/or colony vectors of inoculation.

The present invention further provides these and other advantages with improved control of insect pests using fungal compositions (mycopesticides and mycoattractants) having strong attractant properties and placing these attractant preconidial fungi in or around an object or area to be protected. The present invention also provides insecticidal foods and baits that utilize, as a toxicant, relatively innocuous and naturally occurring materials as the active agent, so as to control insects without undue effect on the ecology. Alternatively, the present invention provides attractants that can be utilized with biocontrol agents, environmentally benign biopesticides, chemical control agents including insect toxicants and pesticides, physical control agents such as mechanical and electrical devices and combinations thereof.

A further advantage is achieved by actively avoiding the use of conidia in that the time and expense of raising conidial stage mycelium and/or separating conidia is rendered unnecessary and avoided.

Still further objects and advantages of the present invention will become more apparent from the following detailed description and appended claims.

Before explaining the disclosed embodiments of the present invention in detail, it is to be understood that the invention is not limited in its application to the details of the particular products and methods illustrated, since the invention is capable of other embodiments, including those embodiments that have not yet been reduced to practice and tested. In addition, the terminology used herein is for the purpose of description and not of limitation.

DESCRIPTION OF THE PREFERRED EMBODIMENTS

Fungi have been recognized as the causative agents of insect diseases and the fungal spores utilized as microbial insecticides for over 100 years. A great deal of ongoing research continues to be directed to the use of spores as mycopesticides; see, for example, U.S. Pat. No. 6,261,553 (2001) to Bradley et al. and U.S. Pat. No. 6,254,864 (2001) to Stimac et al. Attention has continued to be directed to spores as the infectious agent, perhaps because the prevailing paradigm has been that that infection is generally via spores (infective propagules that are termed spores or conidia in Zygomycotina and Deuteromycotina, microconidia in certain entomophthoralean species such as *Conidiobolus cornatus*, zoospores in Mastigomycotina, or plantons or acospores in Ascomycotina, including resting spores) with subsequent spore germination and hyphal penetration of the host body by the fungal mycelium causing insect death. See, for example, U.S. Pat. Nos. 4,925,663, 5,360,607, 5,413,784, 5,683,689 and 6,254,864 and Schmid-Hempel, P., *Parasites in Social Insects*, Princeton University Press, pp. 36, 43-44 (1998). The fungal mycelium itself, particularly that of the Deuteromycetes, has been utilized only as a spore source, whether in the laboratory or in the field.

In contrast to the previous research, the present inventor has found that prior to spore or conidia formation, the preconidial mycelium of entomopathogenic, insect-killing fungal species possesses numerous previously unrecognized properties as an attractant and as a uniquely enticing insect food composition, capable of inducing novel behaviors in the social insects including "grazing" on and "housekeeping" in preconidial mycelium and scattering of the preconidial mycelium around feeding areas and nesting chambers. The preconidial mycelium of virulent strains can act as an infectious agent with numerous vectors of infection and infestation via ingestion and/or contact with further mycelial growth.

The concepts of "pathogens" and "pathogenic" (and the related "entomopathogens" and "entomopathogenic") have implications that extend well beyond the standard dictionary definition of "capable of causing disease or mortality." Some entomopathogenic fungi are widespread and cause no known effects whatsoever in their insect hosts; *Myrmicinosporidium durum* is illustrative of entomopathogenic fungi that cause few symptoms and are consequently hard to detect in the first place. Schmid-Hempel, supra, p. 83 (1998). Entomopathogenic fungi as used herein are those capable of infecting and parasitizing insects, regardless of their actual effect on the host. "Virulence" and "virulent strains" similarly have meanings extending beyond the dictionary definition of extremely infectious, malignant or poisonous. Parasite virulence and host resistance determine how host and parasite interact in ecological time and how they both coevolve. Virulence is often defined as an increase in the host mortality rate as a result of the parasite's presence. But reduced host fecundity, parasite replication rate within the host, and several other measures have also been used. Virulence should in principle also include instances where the behavior of the host is manipulated by the parasite to increase the probability of its successful transmission and where it places the individual host at greater risk. See Schmid-Hempel, supra, pp. 237-238. Here the terms virulent and virulence are used in a broad sense that encompasses all of these meanings. It will refer to processes that are caused by entomopathogenic fungi and which lead to a reduction in some component of the host's fitness or mortality. Virulence and resistance are therefore properties that emerge as a result of host-parasite interaction in a given environment. Expression of virulence is as diverse as the lifestyles and characteristics of the insect hosts and the entomopathogenic fungi themselves. The present invention provides improved mycoattractants and mycopesticides (fungal mycelia utilized as insect attractants or baits and/or insect biopesticides, after mycology, the study of fungi). The attractiveness of fungal mycelia to many species is well known. Black Angus cows have been observed running uphill (a rare event) to reach spent Oyster mushroom mycelium on straw. Cultured mycelia such as Morel mycelium is considered a delicacy when added to human foods; gourmet mushrooms themselves are a structure arising from mycelium to form fruitbodies. Indeed, the attractiveness of mycelial scents is to a great degree responsible for the fresh and refreshing scent of a forest after a rain, a result of the mushroom mycelia responding to the humid conditions with rapid growth. Mycelium is also known to be highly attractive to insects. Certain leaf-cutting ants, termites and wood-boring beetles are known to cultivate and raise fungal mycelium as an exclusive food source (for example, "ambrosia fungi") and mycelium is a preferred food source of many insect species. As discussed above, brown rot mycelium (the mycelial stage of a wood-rotting type of fungus that produces some mushrooms) has been used as an attractant for termites.

However, for use as a "contact insecticide" control agent, application of the fungal entomopathogenic species has typically involved either conidia (spores) or a mixture of conidia and mycelium or mycelium as a spore source in the laboratory or field. Such conidial contact insecticides suffer from at least two major biological disadvantages: 1) conidia and conidia/ mycelium preparations are to some degree unattractive or even repellant to insects; and 2) such conidia preparations are highly dependent on free water or humid conditions and/or specific insect recognition factors for gestation of the spores and infestation during the typical life cycle of an insect fungal control agent. Furthermore, conidia have been found to be more effective against "stressed" insects and/or insect populations than against healthy insects and populations. Laboratory procedures for testing entomopathogenic fungi often involve procedures inapplicable in the field, such as "dusting" of many or all of the insects with spores or forced contact with conidia in petri dishes (itself a form a stress). Insects infected with mycopesticidal spores are often rejected or isolated from the general population, thus limiting the further spreading of the fungal disease. Wilson, E. O., *The Insect Societies*, The Belknap Press of Harvard University Press, pp. 103-119 (1974). For these and other reasons, conidia of entomopathogenic fungi have often been much more effective under laboratory conditions than in the field.

Noting that conidia have been utilized as a repellant for termites, and driven by a desire to avoid contamination of a sterile-culture gourmet and medicinal mushroom laboratory with the spores of mycopesticidal species, further investigation of the preconidial stages of the Deuteromycetes *Metarhizium* and *Beauveria* were undertaken. The preconidial stage is the vegetative stage of the fungus, prior to the formation of structures leading to the release of airborne spores (which is distinguished from fragmentation of hyphae which can become airborne if dried). Those skilled in the art will recognize that mycelia or mycelial hyphal fragments may form structures such as arthrospores (a preconidial structure imbedded within the mycelia) or other nascent spore structures and such mycelium should be considered a "preconidial mycelium" as discussed elsewhere.

It was found that the "fragrance signature" of the mycopesticidal mycelium is a strong attractant to insects prior to conidia formation. The genesis for these findings was the initial observation that the odor of the cultured mycelium was similarly pleasing to humans when preconidial and repellant after conidia formation; smell and the fragrance signatures of mycelium are utilized by the present inventor as indicators of the health of the mycelium in large scale production of gourmet and medicinal mushrooms, whereas "petri dish mycologists" and entomologists studying pathogenic fungi are typically trained not to sniff or inhale from the cultures. It was noted such fragrance signatures are lost when mycelium is grown via liquid fermentation—this may be due to such fragrance signatures being "washed away" or due to the greatly reduced nutritional base available to the mycelium in liquid fermentation as compared to solid substrates such as grain or wood, as "outgassing" of the mycelium of $CO_2$ and attractant molecules is believed by the present inventor to be responsible for at least some portion of the attractant value. It was also noted that liquid fermentation utilizing a typical fermentor with bubbled air mixing will promote conidia formation, with such conidia production being even further promoted by the common commercial practice of utilizing bubbled or chemically generated oxygen.

In addition to the attractant properties and phagostimulatory (feeding stimulating) properties of preconidial mycopesticides, it was further found that pathogenic fungal control agents are much more effective when preconidial (pre-sporulation) mycopesticidal mycelium is ingested and/or contacted by the targeted insect as compared to conidia or post-sporulation mycelium/conidia offered to targeted insects for the purpose of infection by contact. The preconidial mycopesticidal mycelium is thought to be an effective attractant and/or pathogen, at least in part, because it is a preferred food, particularly for social insects and other fungi-feeding insects The preconidial mycelium has been observed to be a preferred food source that stimulates "grazing" of the fungi on wood and/or grain, scattering of the fungus and caching of the fungus by social insects including termites, carpenter ants and fire ants. Novel behaviors observed in the social insects include that of Formosan termites (*Coptotermes formosanus*) ignoring available wood to set up "housekeeping" in the mycelium and fire ants and carpenter ants moving the preconidial fungi around the feeding arena and/or into nest chambers. Social insect colonies have been described as "factory fortresses." Wilson, E. O., supra, and Oster, G. F. and E. O. Wilson, *Caste and Ecology in the Social Insects*, Princeton University Press (1978). While it may be difficult for a parasite to "break into the fortress" and gain access to a colony, once inside, the opportunities abound. Schmid-Hempel, supra, p. 77. Similarly, once the social insect defenses have been penetrated via the attractiveness of preconidial mycopesticidal mycelium, the opportunities abound for further inoculation and spread of the preconidial mycelium both orally and dermally, as well as optional introduction of other biocontrol agents or chemical toxicants. Novel and unique features of the invention include the use of a mycopesticidal mycelium or extract as an attractant, the use of a mycopesticidal vector of parasitization that relies directly on hyphal fragments to infect both insects and/or social insect housing structures, the use of high levels of carbon dioxide to grow and maintain preconidial mycelium, the use of late sporulating strains so as to prolong the attractive preconidial state, the use of various methods to arrest development at the preconidial stage and/or to facilitate growth, packaging, shipping and convenient application by an end user and various improvements in methods of attracting, controlling, preventing, eradicating and limiting the spread of insects.

Preconidial mycelium has proven to be highly effective by ingestion or contact, the mycelial hyphae already being in a state of active growth when ingested or contacted. The preconidial mycelium is thought by the present inventor to function both as a "fungal food of infection" and as a contact insecticide. Efficacy as a contact insecticide is believed to be aided by the somewhat "sticky" nature of mycelium. While not wishing to be bound by any theories or hypotheses, the present inventor believes various possible vectors for further spread and growth of the preconidial mycelium include incidental contact and adhesion, feeding and "sloppy eating" which may spread hyphae to insect cuticles, food caching, individual and social grooming, aerial transmission of hyphal fragments (as dry hyphal fragments are much less dense than spores, they easily become airborne and spread), inhalation, incidental contact, trophallaxis (exchange of liquid food), proctodeal trophallaxis (exchange of anal excrement by termites and others), cannibalism, mating, contact with cadavers, inoculation of housing structures, etc. Mycopesticidal species are thought by the present inventor to employ various pathogenic modes when transmitted via ingestion or contact with mycelial hyphae—for example, infection via the cuticle, the tracheal openings, the alimentary canal or wounds with resultant growth upon the insect and resultant depletion of host resources and/or damage or destruction of host tissue, production of antibiotics, antibacterials and antiprotozoans with the resultant death of microflora within the gut, production of anti-fungal compounds affecting symbiotic and associated fungi, production of toxic substances by the entomopathogen, suppression or disruption of the immune system response, etc. The mycelial hyphae may also inoculate the excavations and/or organic debris housing structures (such as the termite mounds of wood or varying plant materials and debris cemented with salivary or fecal secretions) of social insects. As the social insects disrupt and distribute the individual particles of mycelium throughout the colony, the mycelium is selectively encouraged to continue to grow in a preconidial state, delaying the time to sporulation, as the fragments of hyphae re-grow upon encountering new food sources. Hence another advantage to this invention is the further delaying of sporulation by the targeted insect colony, thus insuring full inoculation of the nest.

Furthermore, whereas conidial preparations are more dependent upon humidity in the insect environments, attractant preconidial mycopesticidal mycelium which is eaten or contacted by an insect is dependent in some part only upon the humidity in the immediate vicinity of the mycelium, the humidity of the mycelium of course being much more easily controlled than that in the wider general insect environment. The microenvironment "on" an insect is likely more conducive to hyphal growth than to spore germination, with hyphal growth typically being more immediate among fungi than spore germination. Optimal humidity conditions (often very high) and temperatures (depending on the type of fungus) are necessary for germination, and the process is also sensitive to the presence of secreted substances on the host's body surface, e.g., fatty acids and other fungicidal substances. Schmid-Hempel, supra, p. 36 and the references cited therein. Fungi may also enter through the alimentary tract as known from *Beauveria bassiana* in the fire ant *Solenopsis* and in termites. However, the hyphae enter the body cavity some 72 hours after ingestion of spores, and the chemical environment of the alimentary tract may be very aggressive and destroy the growing hyphae, although tracheal openings are an obvious target. Schmid-Hempel, supra, pp. 36, 43-44. Fungal spores are not always infective if ingested by ants because of a filter apparatus established by the infrabuccal cavity and/or the proventriculus just in front of the stomach. Schmid-Hempel, p. 106. On the other hand, it has been recognized that with the exception of a few Entomophthorales, all entomopathogenic species can be cultured on artificial media, and are therefore facultative rather than obligate parasites even though they may be obligate symbionts or pathogens in the ecological sense if they have no capacity for free-living existence, other than as propagules, in the absence of a suitable host. Keller, S, and K. Zimmermann, Mycopathogens of Soil Insects, in Wilding et al. (eds.), *Insect-Fungus Interactions: 14th Symposium of the Royal Entomological Society of London in collaboration with the British Mycological Society*, Academic Press, pp. 250-251 (1989). Although preliminary experiments reveal that *M. anisopliae* is a poor competitive saprophyte, (Zimmermann, supra, unpublished, evidently with spores), the present inventor has found both *Metarhizium* and *Beauveria* to be facultative saprophytes that do quite well on grain and wood in the preconidial stage when cultivated under standard sterile mushroom growing conditions. This saprophytic ability, coupled with the "mycelial momentum" the present inventor has observed in fungi in general, indicates that preconidial mycelium may thus present numerous advantages that have not been heretofore observed, such as higher transmission rates and effectiveness toward targeted pest insects where mortality has not been previously observed due to failure of spores to adhere and germinate or other virulence factors. The mycopesticidal life cycle stage of spore germination is skipped entirely via utilization of preconidial mycelium, with hyphal growth in or on an insect commencing directly. Furthermore, as social insects spread mycelium throughout the colony, nestmates and the feeding and nesting chambers may become inoculated. As the mycelium permeates the surrounding habitat, resident moisture increases as a direct consequence of the sponging and transporting properties of the mycelium. In doing so, more mycelium grows, increasing the effectiveness of this method. As an additional benefit, the mycelium may dry out and become "reactivated" by humid conditions, thus functioning as a prophylactic and preventative treatment and long-term protectant.

Because mycopesticidal mycelium as a food or ingested mycelium seems to take longer for parasitization by the fungi to become obvious to a social insect colony as compared to spore germination on an external site, the time for the colony to recognize and isolate infected individuals is similarly prolonged, with the result of infectious spread throughout the colony before the defensive mechanisms of social insects can react to infected individuals and maturing hyphae. As the delay is increased, there is correspondingly less likelihood of learned responses and quarantine of infested individuals or colony chambers.

It has been found by the present inventor that the preconidial stage can be maintained in many mycopesticidal strains provided carbon dioxide ($CO_2$) levels are maintained above the approximately 365 ppm of carbon dioxide currently found in the atmosphere, to with: at an elevated level, e.g., 500 ppm. The $CO_2$ levels preferably range from 2,000 ppm, preferably 6,000 ppm, more preferably 10,000 ppm. The upper concentration of $CO_2$ is preferably not more than 200,000 ppm, more preferably not more than 100,000 ppm, and most preferably not more than 50,000 ppm in air. Once exposed to fresh air, the mycelium of many strains can produce conidia in just a few days. By preventing conidial formation, the mycelium continues to accumulate mycelial biomass (sans conidia). This prevention of conidia formation is a central component in this technology, as conidia formation is thus actively avoided. Strains that do not sporulate under elevated carbon dioxide conditions after overgrowth of the substrate for at least 1, and preferably 5 additional days after overgrowth are preferred, more preferably those that do not sporulate for 10 additional days, and most preferably those that do not sporulate for 60 days, or more. Thus, for example, *Metarhizium anisopliae* #62176 has been observed to maintain a preconidial state in spawn bags with filter patches for 35 days or more after overgrowth, and *Beauveria bassiana* #20872 and 70438 have been observed to maintain a preconidial state for 60 days. Strains that do not sporulate for at least three days after exposure of the preconidial mycelium to air and/or dirt are preferred, those strains that do not sporulate for at least seven days are more preferred, while still more preferred are strains that do not sporulate for at least 10 days, or most preferred are strains that do not sporulate for 21, or more, days. Thus, even after overgrowth of the substrate in the cultivation container, the mycopesticidal mycelium may be maintained in a preconidial state via elevated carbon dioxide levels and/or refrigeration at 1-10 degrees C. and maintained in a preconidial state after exposure to the elements.

Mycopesticidal mycelium is grown in pure culture using standard fermentation techniques well established for in vitro propagation of mycelium from mycelium or spores. For example, the fermented mycelia is diluted and transferred into a sterilized grain or a mixture of sterilized grains (rice, wheat, rye, oat, millet, sorghum, corn, barley, etc.); alternatively, mycelia may be cultured on a petri dish (from mycelium or spores) and transferred to grain or other standard techniques may be utilized. The grain is pressure steam-sterilized at one (1) kg/cm$^2$ (15 psi) for 30 minutes to several hours, depending upon processing parameters such as mass to be sterilized, type of autoclave, compartmentalization and other factors. The master broth is transferred aseptically manually or by using peristaltic pumps into the sterilized grain. Alternatively, growth mediums of or containing wood (including bait chips and bait traps), sawdust and/or wood chips, agricultural wastes, cardboard, paper, fiber blankets or other cellulose-containing substances may be utilized for cellulose loving insects (including termites and carpenter ants). A variety of containers are used for incubation, including high-density polyethylene and polypropylene bags, glass and polypropylene jars, metal containers, etc. Use of such containers provides a convenient method of maintaining high carbon dioxide levels, as the growing mycelium gives off $CO_2$. Carbon dioxide levels will rise to acceptable levels for use in the present invention even if filter patches, disks or materials are utilized to allow some gas exchange. Alternatively, grow rooms may be maintained at high $CO_2$ levels. Further information on such culture techniques, including information of the selection and isolation of species, strains, varieties and sectors of cultures may be found in the applicant's books, *Growing Gourmet and Medicinal Mushrooms*, Ten Speed Press (1993, 2000) (Library of Congress Card Catalog Number SB353.S73 2000) and *The Mushroom Cultivator*, Agarikon Press, (1983) (with J. Chilton) (Library of Congress Card Catalog Number SB353.S74 1983), hereby incorporated by reference.

Once inoculated, the mycelia on grain (or on wood or other cellulosic, ligninic, celluloligninic or carbohydrate containing substrate or other natural or artificial substrate) matures to a state prior to conidia formation and may be utilized fresh or metabolically arrested or developmentally arrested through flash chilling (freeze-drying), drying, refrigeration, cooling via nitrogen, carbon dioxide, or other gasses, absence of light, or control by other means. It will be understood that such metabolic arresting of development may encompass either a slowing of metabolism and development (such as refrigeration) or a total suspension or shutdown of metabolism (freeze-drying, air-drying and cryogenic suspension). When freeze-drying, drying or other known methods of arresting development are utilized, it is essential that freeze-drying or other methods occur at the stage in the life cycle of these fungi before the spores are produced. The mycelium-impregnated grain media may then be fragmented and packed in appropriate containers for commerce. Fresh, dried and freeze-dried materials may also optionally be enhanced by use of protectants and nutrients (sugars are one preferred material that have both protectant and nutrient qualities), and materials such as wetting agents, surfactants and surface active agents, dispersants, emulsifiers, tackifiers or adhesives, penetrants, fillers, carriers, antibiotics, germination enhancers, growth enhancers, carbohydrates, nutritional supplements, spore and hyphae encapsulating materials, yeasts, bacteria, fungi perfecti and imperfecti, etc. Alternatively, fresh, dried or freeze-dried preconidial material may be utilized within a cellulose-containing or starch sheath or coating for enhancing the effectiveness as a delivery system, and for attracting cellulose-consuming insects. Fresh mycelium may be shipped in growing containers such as jars or spawn bags, which allows easy maintenance of a high carbon dioxide atmosphere and maintenance of sterile conditions during shipping.

When the freeze-dried or dried mycelium is reactivated via rehydration, the mycelium is typically preferably allowed to slowly rehydrate through controlled absorption of atmospheric humidity, with the result that the mycelium "wakes up" and wicks into the air. This is a very different response from immersion, which often results in bacterial contamination and souring, as the freeze-dried mycelium of some, but not all, mycopesticidal species suffers when immersed in water. Such rehydration and reactivation may be carried out on a large scale through high humidity atmosphere, or may be accomplished by an end user through use of wet materials such as sponges, wicking materials and/or other evaporative materials or by atmospheric absorption of humidity from a remote water reservoir. Such end user rehydration may be carried out in any suitable container or a bait box if desired. Where species or strains do not respond adversely to water saturation, immersion or other saturation or partial saturation techniques may be utilized. Warming is suitable for reactivation of refrigerated materials; it is preferred that the mycelium not be refrigerated for extended lengths of time.

Particularly preferred are those strains that are slow to sporulate (i.e., late conidia formers, thus prolonging the preconidial stage) both before and after exposure to air and/or dirt that additionally possess the desired characteristics of attractiveness to the targeted insect, virulence and pathogenicity (or lack thereof), low mortality rate of non-targeted insects, time to insect death, mortality rate for virulent strains, the proportion of kill of each life stage of target insects such as larvae, pupae, workers, soldiers and royalty, high transmission rates, host specificity for targeted insects, growth rate and speed of colonization of substrates, sensitivity and response to high and low carbon dioxide levels, recovery from drying, freeze-drying, refrigeration or other forms of metabolic arrest, recovery from transportation, stress tolerance, preferred temperature and humidity conditions matched to insect ecology and abiotic conditions, microflora sensitivity, ability to surpass competitors, adaptability to single component, formulated and complex substrates, high production of attractant essences and extracts, genetic stability/instability, post-sporulation pathogenicity and virulence, etc. The interaction between mycopesticidal fungi and their insect hosts is complex and dynamic and no single trait or component of the invasion process is likely to determine virulence (or pathogenicity). Virulence also may be determined by environmental factors—as some mycopesticidal species are known to become non-virulent when cultured on non-insect media, such cultured species are likely to become more virulent as the preconidial mycelium spreads via social grooming, incidental contact, contact with cadavers, etc. Those skilled in the art will recognize that such virulence characteristics can be selected for utilizing known techniques and bioassays.

As the preconidial or pre-sporulation mycelium is an attractant whereas the conidia spores are more or less repellant, most preferred would be "sporeless" or "slow-to-sporulate" strains of mycopesticidal fungi.

To select an entomopathogenic species, strain or variety or sub-strain, or to select for a characteristic within those species, strains, varieties or sub-strains, or to isolate and propagate cultures involves choices that affect the downstream methods, products and activities. Such selection might involve location and isolation of a species or strain from the wild or the acquisition from a culture bank or other source, the selection of a petri dish culture which manifests the desired characteristics, the selection of a strain which gives favorable results in a bioassay or the selection of a sector within a petri dish culture for healthy growth or other characteristics. If selecting for slow to sporulate strains or sub-strains, one would choose to culture out those sectors displaying the preconidial mycelium rather than those sectors displaying post-conidial mycelium.

More than one fungus and/or substrate can be used to create a matrix of characteristics to increase usefulness as a natural pesticide and maximize effectiveness against an individual or a diverse population of economically or ecologically damaging insect species. For example, a plurality of *Beauveria, Metarhizium, Paecilomyces, Verticillium*, and/or *Cordyceps* species and strains might be utilized, a mixture of grains of various sizes might be utilized and/or a mixture of various grain and cellulosic substrates might be utilized. Grains may be selected based on such factors as an insect's mandible size, preferred food particle size, insect size and size of grains that the insect may grasp and/or carry, insect preference, similarity to pupae, etc. Woods and the wide variety of cellulosic materials may similarly be selected based on insect preferences; for example, birch and pine are preferred woods of many insects. Attractant properties may vary between species and with each strain, also affected by type of grain or carrier material (wood blocks) and various other factors, and mycopesticidal strains may be selected for peak attractant properties on particular cellulosic substrates as well as attractant properties in general.

In utilizing wood and other cellulose containing materials, one preferred method is to grow the pre-sporulation mycopesticidal mycelium on wooden or other cellulosic materials "bait blocks" or "bait traps." Bait chips, blocks or traps (or optionally other forms such as pellets, extruded pellets, mats, fabrics, ropes, etc.), optionally soaked with a malt solution or other sugar and/or nutrient solution, are infused and/or inoculated with preconidial mycopesticidal mycelia which then spread the infection to the targeted insect pests via any of the mycelium vectors described herein. Biodegradable bait traps may be made of, or have components made of, various cellulosic, ligninic, cellulolignic, carbohydrate and fiber materials including but not limited to paper products and cardboard, wood and sawdust, corn cobs and cornstalks, chip board, jute, flax, sisal, reeds, grasses, bamboo, papyrus, coconut fibers, nut casings such as peanuts, almonds, walnuts, sunflower, pecans, etc., seed hulls such as cottonseed hulls, hemp, cereal straws, sugar cane bagasse, soybean roughage, coffee wastes, tea wastes, cactus wastes, banana fronds, palm leaves, fiberized rag stock, combinations thereof, and numerous other forest and agricultural products and byproducts which will host mycelium and are degradable by mycopesticidal fungi. Where rapid biodegradability of the traps is desired, materials such as cardboard or paper may be utilized. For insects including carpenter ants or termites, cockroaches, etc., the bait blocks preferably contain channels, tunnels, grooves, ridges, holes, or perforations specifically sized to allow entry by the targeted species and or its brood, pupae and/or larvae. Inoculation may, for example, be accomplished via grain in the channels and the blocks may optionally be layered or "wafered" together. A composite, layered or intertwined matrix of materials may be utilized, with one set of materials infused with the attractant extract of an entomopathogenic species and the other containing active or metabolically arrested preconidial mycelium. A multiplicity of such bait blocks or traps or barriers may be utilized to protect structures, agricultural locations, etc. A fungal matrix with a plurality of pre-sporulating mycopesticidal fungal species and/or extracts that are highly attractant to the targeted pest insect may be created so that the targeted pest is drawn close to a locus where the insect pest becomes infected and is harmed or killed by the selected fungi or via other means.

The wooden or cellulose baits and bait traps may optionally be dried or freeze-dried. Either the myceliated bait may be presented to the insect, with rehydration and recovery taking place, for example, within the central nests of social insects, or the wooden bait block may be rehydrated prior to or during use.

The highly attractive nature of preconidial mycopesticidal mycelium indicates that essences extracted from preconidial mycelium of mycopesticidal fungi can be expected to be highly attractive in and of themselves, and thereby similarly useful alone or in conjunction with biological, chemical, mechanical and/or electronic insect control agents, useful as masking agents for otherwise repellant toxicants for insect pests, and useful as "distractants" in diverting insects away from sites that need protection. Such essences include extracts, concentrates, fragrances, derivatives, active constituents, etc. and may be prepared by methods known to the art including extraction with water, alcohols, organic solvents and supercritical fluids such as $CO_2$, etc. Extracts may also be prepared via steam distillation of volatile components, similar to the preparation of "essential oils" from flowers and herbs. Suitable alcohols include those containing from 1 to 10 carbon atoms, such as, for example, methanol, ethanol, isopropanol, n-propanol, n-butanol, 2-butanol, 2-methyl-1-propanol (t-butanol), ethylene glycol, glycerol, etc. Suitable organic solvents include unsubstituted organic solvents containing from 1 to 16 carbon atoms such as alkanes containing from 1 to 16 carbon atoms, alkenes containing from 2 to 16 carbon atoms, alkynes containing from 2 to 16 carbon atoms and aromatic compounds containing from 5 to 14 carbon atoms, for example, benzene, cyclohexane, cyclopentane, methylcyclohexane, pentanes, hexanes, heptanes, 2,2,4-trimethylpentane, toluene, xylenes, etc., ketones containing from 3 to 13 carbon atoms such as, for example, acetone, 2-butanone, 3-pentanone, 4-methyl-2-pentanone, etc., ethers containing from 2 to 15 carbon atoms such as such as t-butyl methyl ether, 1,4-dioxane, diethyl ether, tetrahydrofuran, etc., esters containing from 2 to 18 carbon atoms such as, for example, methyl formate, ethyl acetate and butyl acetate, nitriles containing from 2 to 12 carbon atoms such as, for example acetonitrile, proprionitrile, benzonitrile, etc., amides containing from 1 to 15 carbon atoms such as, for example, formamide, N,N-dimethylformamide, N,N-dimethylacetamide, amines and nitrogen-containing heterocycles containing from 1 to 10 carbon atoms such as pyrrolidine, 1-methyl-2-pyrrolidinone, pyridine, etc., halogen substituted organic solvents containing from 1 to 14 carbon atoms such as, for example, bromotrichloromethane, carbon tetrachloride, chlorobenzene, chloroform, 1,2-dichloroethane, dichloromethane, 1-chlorobutane, trichloroethylene, tetrachloroethylene, 1,2-dichlorobenzene, 1,2,4-trichlorobenzene, 1,1,2-trichlorotrifluoroethane, etc., alkoxy, aryloxy, cyloalkyl, aryl, alkaryl and aralkyl substituted organic solvents containing from 3 to 13 carbon atoms such as, for example, 2-butoxyethanol, 2-ethoxyethanol, ethylene glycol dimethyl ether, 2-methoxyethanol, 2-methoxyethyl ether, 2-ethoxyethyl ether, etc., acids containing from 1 to 10 carbon atoms such as acetic acid, trifluoroacetic acid, etc., carbon disulfide, methyl sulfoxide, nitromethane and combinations thereof. Extracts may also be prepared via sequential extraction with any combination of the above solvents. The extracts may optionally be combined with fixatives, enhancing agents, oils, alcohols, solvents, glycerin, water and other substances that aid in distributing the attractant and/or enhancing its fragrance value. Essences extracted from preconidial mycelium of mycopesticidal fungi can be used as a protectant or distractant, luring insects away from a locus and preventing insect damage to a locus, habitat, structure, crop, animal, human, etc. Such attractant essences and extracts may be utilized with wicking agents, sprayers, etc. to enhance their effectiveness. Preliminary indications are that such attractant molecules are polar and thus best extracted with polar and/or hydrophilic solvents. The present invention in conjunction with the principles of chemical ecology and evolutionary biology raise the possibility that the entomopathogenic fungal species produce attractant molecules (or more likely, groups of attractant molecules) that have coevolved over evolutionary time with species of insects or groups of insects. Such attractant molecules, optimized for one species of insect, may well show attractant properties to larger groups of insects. It will be apparent to those skilled in the art that numerous such molecules or groups of attractant molecules may be isolated and/or characterized from the preconidial fungi of the present invention and as such should be considered part of the present invention.

The preconidial mycelium or extracts thereof may be utilized solely as an attractant for various purposes. For example, preconidial mycelium may be utilized to affect insect choice of geographical location, destructive pests being attracted and distracted away from structures, agricultural plots, etc. Fungal species and strains particularly attractive to beneficial insects may be utilized to attract desired insect species, the fungi acting as a biological catalyst to steer the course of the insect community evolution. Alternatively, varying insects may simply be attracted to occupy the environment and thus forestall pest invasions. It is known that virulence of entomopathogenic strains varies widely in the laboratory when tested via typical conidia based assays, with mortalities from 0% to 100% being recorded dependent upon such factors as number of conidia applied per insect and the insect species and the entomopathogenic species and strain being tested (see, for example, the U.S. patents above). Similar results may be expected for preconidial formulations, although a greater effectiveness in general may be expected since lack of virulence in the typical bioassay is often related to a failure of conidia to adhere to the insect and/or failure of the conidia to germinate as discussed above. Thus strains of "pathogenic" or "entomopathogenic" fungal species may be selected which actually vary in virulence from non-pathogenic to relatively weakly virulent to strongly virulent. Non-virulent preconidial mycelium may be used to attract beneficial predator and parasitic insects. Alternatively, non-virulent strains may be utilized as a distractant, for example attracting Coccinellidae, the lady beetles, away from areas where they may be a pest (such as office buildings) and into "ladybug motels." Alternatively, virulent strains may be utilized as an olfactory attractant but made inaccessible with devices such as screens or slots.

The mycoattractants and/or mycopesticides disclosed herein may also be optionally enhanced by the use of other baits, foods, attractants, arrestants, feeding stimulants, sex pheromones, aggregating pheromones, trail pheromones, etc. For example, a bait box overgrown with preconidial mycopesticidal mycelium might contain other attractants and contact pesticides.

Attractant preconidial or pre-sporulation mycelium (virulent, weakly virulent and/or non-virulent) or extracts may also be utilized in conjunction with other biological organisms, chemical pesticides and physical control agents as part of integrated pest management (IPM) systems that incorporate multiple pest control tools and seek to minimize pesticide inputs. The use of attractant fungi in combination with other insect control agents affords the advantage of attracting the targeted pest to a locus which, by other treatments, results in sterility and/or death of the targeted insect.

The weakened immune systems of pest insects exposed to pathogenic or virulent mycopesticidal organisms allows other beneficial parasitic and predator species to flourish. Such beneficial biological control agents include microbial pathogens, predator insects (entomophagous insects which eat other insects) and parasitic insects (those which reproduce by laying eggs in or on any stage the host insect, from egg to adult), as well as non-insect predators such as birds and beneficial nematodes, spiders and mites. Examples of biological control agents include entomopathogenic fungal species and their spores, *Bacillus thuringiensis, B. popilliae* and *B. subtillis* and *Pseudomonas*, fire ant parasites (such as Phorid flies), fly parasites (wasps such as *Muscidifurax raptorellus* and *Spalangia cameroni*), hister beetles such as *Carcinops pumilio*, dung beetles including *Onthophagus* spp., parasitic nematodes such as *Steinernema feltiae*, cockroach parasites (*Anastatus tenuipes, Aprostocetus hagenowii, Comperia merceti* and nematodes), lacewings, ladybugs, bigeyed bugs, damsel bugs, praying mantises, *Trichogramma* wasps, beneficial mites, ant parasites, flea parasites, lygus bug parasites, mealybug, aphid and whitefly parasites and predators, caterpillar parasites, spider mite predators, looper parasites, diamondback and moth parasites, scale parasites and predators, mite parasites and predators, etc. Strains may be selected, utilizing those methods known to the art, for virulence against the targeted pest insects and/or non-virulence or weak virulence against predator insect species as well as such qualities as resistance to pesticides, etc. If desired, resistant predator or parasitic species may be selected for, bred and released to further control the targeted pest species. Blends of beneficial insect attractant plants and habitat plants may also be utilized. This dualistic approach is not limited to just one pairing of fungus and beneficial organism as many pairings could be implemented for the purpose of creating an environmental equilibrium affording long-term protection. Other fungal attractants may also be optionally utilized. Thus, a combination of the preconidial mycelium of mycopesticidal species and Oyster mushrooms (*Pleurotus* and *Hypsizygus* species, the mycelium and mushrooms of which are very attractive to Phorid flies) might be utilized to attract phorid flies in the genus *Pseudacteon* that parasitize fire ants and leaf-cutter ants.

The preconidial mycopesticides (both virulent and non-virulent strains) and extracts may also be utilized as "masking agents" as well as attractants in conjunction with insect chemical control agents, toxicants and/or pesticides, thereby preventing aversion to other effective compounds that may otherwise repel the insect. Chemical control agents include insect toxicants, poisons, regulators and pesticides as well as the chemicals (semiochemicals) which mediate interactions between individuals of a insect species (pheromones) or between co-evolved species (allelochemicals, such as kairomones and allomones). Residual (persistent), non-residual (nonpersistent) and solid, liquid, aerosol or fog contact chemical control agents include, by way of example but not of limitation, stomach poisons such as sulfluramid, pyrethrum extracts, natural and synthetic pyrethroids, parapyrethroids (non-ester pyrethroids) such as silafluofen, etofenprox and cyfluthrin, pyrethroid analogs such as fenvalerate, permethrin, phenproparthrin, fluvalinate, flucythrinate, fenproparthrin, cypermethrin, deltamethrin, tralomethrin, cyclopro-thrin, esfenvalerate and zeta-cypermethrin, allethrins, lethanes, nicotinyl compounds such as imidacloprid, phenylpyrazoles such as fipronil, amidinohydrazones such as hydramethylnon (a respiratory poison), abamectin (a mixture of avermectins, insecticidal or anthelmintic compounds derived from the soil bacterium *Streptomyces avermitilis*), Spinosad (spinosyn metabolites produced by *S. spinosa*), nitromethylenes, carbamates such as propoxur and fenoxycarb, organophosphates such as acephate and chlorpyrifos, pyriproxyfen, insect growth regulators, synthesis inhibitors, chitin synthesis inhibitors such as hexaflumuron and diflubenzuron, mineral acids such as boric acid, alcohols and organic solvents, elements such as sulfur and combinations thereof. Such chemical control agents may optionally be combined with synergists compounds that increase the toxicity and/or enhance the biological activity of another, for example by inhibiting the enzymatic detoxification of insecticides by microsomal oxidases or hydrolytic enzymes such as esterases. Examples of synergists include methylenedioxyphenyl (MDP) compounds such as piperonyl butoxide, piperonal bis-(2,2-(butoxyethoxy)-ethyl)acetal, 1,2-methylenedioxynaphthalene, tropital (polyalkoxy acetal of piperonaldehyde) and sesamex, trisubstituted aliphatic and aromatic phosphates such as TOCP (tri-o-cresyl phosphate), a number of non-insecticidal carbamates, EPN (O-ethyl-O-p-nitrophenyl phenylphosphonothionate), sulfoxide, propynyl ethers, p-nitrobenzyl thiocyanate, 2-((4,6-dichloro-2-biphenylyl)-oxy)triethylamine, 2-(diethylamino)ethyl 2,2-diphenyl pentanoate, 2-propynyl 4-chloro-2-nitrophenyl ether, N-octyl bicycloheptane dicarboximide and n-propyl isome. Use of attractant or attractant/pesticidal preconidial mycelium or extracts enables the use of extremely small amounts of toxicant or pesticide to effectively control insect populations. Alternatively, sublethal doses of pesticides or toxicants may be included to enhance the activity and virulence of the mycopesticidal species; or pathogenic and virulent preconidial mycelium may be utilized as a preconditioning treatment, increasing the susceptibility to and/or potentiating the virulence of other agents (such as pesticide chemicals, other mycopesticides, or bacteriological, plasmodial and viral compounds). Lethal or sublethal doses of insect toxic materials may optionally be encapsulated within an attractant extract- or mycelia-impregnated (virulent or non-virulent) sheath, coating, covering, encapsulative material, protective and/or time degrading envelope, or the toxin may surround, cover or encapsulate a mycelial substance or extract of strong attractive and/or mycopesticidal properties, or such may be simply mixed.

The mycoattractants and mycopesticides of the present invention may also be combined with physical control agents. Physical control agents are devices that destroy insects directly or act indirectly as barriers, excluders, or collectors. Physical controls include the use of mechanical and electrical devices, heat, light, electricity, X-rays, and so on, to kill insects directly, reduce their reproductive capacity, or to attract them to something that will kill them. Various physical means may be employed to act as barriers to insect movement. Sticky materials in which insects become hopelessly entangled may be used in the form of flypaper or coated objects and materials. Traps may be used for control, survey, and surveillance purposes. Control traps may be used in conjunction with mycoattractants and with some means of killing the insects that enter (e.g., a pesticide or an electrically charged grid).

The preconidial mycelium on manufactured, compressed pellets or granules, with or without additional liquid(s), can be used for applications in agricultural, forest, industrial and/or domestic settings, wherein the myceliated pellets become a loci for attracting the target pests, and thus through contact become infected. Trends in mushroom spawn for gourmet and bioremediation purposes have long been evolving towards pelletized or granular spawn while mycopesticidal spore technology similarly has evolved toward granulated or spray formulations. Various forms of pelletized spawn, coated compositions, granules and dusts are known, including those formed from nutrients, with or without carriers and binders, such as peat moss, vermiculite, alginate gel, wheat bran, calcium salts, hydrophilic materials such as hydrogel, perlite, diatomaceous earth, mineral wool, clay, polymers, biopolymers and starch, including wettable powders, emulsifiable concentrates, starch and/or biopolymer coatings, etc. Pelletized spawn is specifically designed to accelerate the colonization process subsequent to inoculation. Idealized pelletized spawn seeks a balance between surface area, nutritional content, and gas exchange and enables easy dispersal of mycelium throughout the substrate, quick recovery from the concussion of inoculation, and sustained growth of mycelium sufficient to fully colonize the substrate. See Stamets, supra, pp. 141-142 and U.S. Pat. No. 4,551,165 (1985), U.S. Pat. No. 4,668,512 (1987), U.S. Pat. No. 4,724,147 (1988), U.S. Pat. No. 4,818,530 (1989), U.S. Pat. No. 5,068,105 (1991), U.S. Pat. No. 5,786,188 (1998) and U.S. Pat. No. 6,143,549 (2000). Liquid sprays include the above wettable powders and emulsifiable concentrates, water-dispersible granules, aqueous solutions, emulsions such as oil-in-water and water-in-oil emulsions, dispersions, suspoemulsions, microemulsions, microcapsules, etc. Wettable powders are formulations that are typically uniformly dispersible in water and also contain surface active agents (surfactants) such as wetting agents, emulsifiers and dispersing agents. Emulsifiable concentrates are prepared with organic solvents and/or one or more emulsifiers. Sticking agents such as oils, gelatin, gums, tackifiers and adhesives may be used to improve the adhesion of the spray. Humectants may also be used to decrease the rate of evaporation, including for example glycols having from 3 to 10 carbon atoms and glycerin and solutes such as salts or sugars in water.

The preconidial mycopesticidal mycelia of the current invention may also be applied as a protectant for equipment. For example, mycopesticidal mycelium may be grown on an organic or organic/synthetic covering such as a sheath or membrane made with a matrix of organic materials such as paper, cardboard, hemp, agricultural fibers, wood, etc., with or without non-degradable materials, and utilized fresh or dried as appropriate. Such mycopesticidal sheaths may be utilized as a preventative barrier to protect electrical cables and wires, computer cables, telephone wires, microwave equipment, optical networks, etc. from damage by fire ants, which can be attracted by electrical activity. Such mycopesticidal coverings in conduits, ducts, corridors, etc. could be activated by decreasing air flow and/or increasing humidity, depending on application, thus allowing dried mycelium to rehydrate and "reawaken" so as to deal with insect outbreaks. Such a solution might have helped save the now-abandoned Superconducting SuperCollider project in Texas from the devastation caused by fire ants that damaged the electrical wiring.

For large scale application, fabric or fiber cloths, landscaping cloths, geofabrics, soil blankets and rugs, mats, mattings, bags, gabions, fiber logs, fiber bricks, fiber ropes, nettings, felts, tatamis, bags, baskets, etc. made of biodegradable materials infused with preconidial mycelia of mycopesticidal species may be utilized as a mechanism for attracting, preventing, killing or limiting the spread of targeted insects (or of attracting beneficial insects). Thus, for example, barriers or "aprons" of mycopesticidal mycelium grown on straw, coconut fiber, wood, paper, cardboard or the other forestry and agricultural products, wastes and cellulose sources noted above might be placed around Oak trees to protect from beetles and introduced wilts such as *Phytophthora* and *Ceratocystis fagacearum* or around pine trees or stands to protect from destructive fungi carried by bark beetles. Similarly, such mycopesticidal aprons might be utilized to protect other trees, shrubs, grasslands, rivers and streams, estuaries, riparian zones, agricultural fields, gardens and crops, structures, communities, habitats and sensitive ecosystems. Such preconidial mycopesticidal aprons might alternatively be used to attract pest insects to a site whereupon other biological, chemical, mechanical, electrical and/or other insect reducing treatments become more effective. Conversely, creation of buffers utilizing non-virulent strains selected for attractiveness to beneficial insects can be used to attract beneficial species which naturally parasitize problem insects.

Alternatively, woodchips, grains, hydromulch and other substrates infused with preconidial mycelium may be utilized in spray hydroseeders or mobile hydroseeders. Agricultural equipment may be utilized to inoculate fields and agricultural wastes. The mycopesticidal fungi may also optionally be utilized in conjunction with saprophytic fungi and mycorrhizal fungi to enhance soils and agricultural yields ("companion cultivation" of beneficial fungi). Mycopesticidal species are also useful in the mycoremediation (fungal bioremediation) of various sites. As one example, reclaimed logging roads could become perimeter-barriers which could forestall and/or prevent beetle-plagues from devastating forestlands by infusing mycomats or hydromulches with species-specific pathogenic fungi (and optionally saprophytic and mycorrhizal fungi), while simultaneously retaining other benefits of mycofiltration. Thus, mycopesticidal species such as *Metarhizium, Beauveria* and *Cordyceps*, mycorrhizal mycopesticidal fungi such as *Laccaria*, and myconematicidal saprophytic fungi such as *Pleurotus* might be combined with ectomycorrhizal and endomycorrhizal species and saprophytic fungi to provide simultaneous insect control, road reclamation and protection of streams from silt runoff. As *Hypholoma capnoides*, a premier wood chip decomposer, mycelium has been observed to be repellant to insects, stretches of insect repellant barriers may be combined with attractant mycopesticidal kill and/or control zones for insects such as wood-boring beetles. Similarly, control of agricultural runoff utilizing saprophytic fungi on agricultural wastes might be combined with the present mycoattractant and/or mycopesticidal applications.

Another approach may optionally be taken with the removal of diseased trees via utilizing chain saw oil as a carrier for mycopesticidal species. In this particular application, conidia or a mycelium/conidia mixture may be utilized as well as preconidial mycelium. Spores and/or mycelium of mycopesticidal fungi, for example *Metarhizium, Beauveria* and/or *Cordyceps*, are infused into chain saw oils so that when the infected trees are cut for removal, the remaining stumpage is inoculated with the mycopesticidal spores and/or hyphae, thus preventing or lessening insect invasions. As another example, a similar approach could be utilized to create "mycopesticidal barriers" in forested lands where boring beetles are a major cause of disease. Such spored or hyphal oils may also be employed in applications such as ecological rehabilitation and mycoremediation. Chainsaw lubricants ("bar and chain" oil) and lubricating oils suitable for the practice of the present invention include petroleum and mineral oil lubricants, including natural bright stock and neutral stock oils, synthetic or semi-synthetic oils, vegetable lubricants and modified vegetable lubricants, animal lubricants and blends and combinations thereof, with or without additive packages. Suitable commercially available biodegradable lubricants include STIHL® BIOPLUS bar and chain oil (natural oils in combination with natural polymers, 99% vegetable-based canola oil), CASTROL® BIOLUBE 100, and vegetable oil lubricants such as those disclosed in U.S. Pat. No. 5,888,947 to Lambert et al., herein incorporated by reference. In general, where oils are utilized, biodegradable oils are preferred as offering a more readily available nutritional source to a wide variety of fungi. The fungal hyphae or spores may optionally be supplemented with further amendments including germination enhancers, growth enhancers, sugars, nutritional supplements, surface active and wetting agents, spore and hyphae encapsulating materials, yeasts, bacteria, fungi perfecti and imperfecti, etc. Fungal hyphal mass can optionally be dried or freeze-dried and packaged, with or without additional spores, in spoilage-proof containers for marketing to end users as an additive. Fresh mycelial hyphae or mycelial mass is best used immediately rather than stored for long periods.

By adding spores of mushroom fungi such as *Hypholoma capnoides* or other insect-repulsive species into chain saw oils, the resultant mycelium growing through the cuts in the dead wood repels pine beetles and other boring insects, thus limiting further infection. By using attractant mycopesticidal species in conjunction with repellant fungal species in another area, a selective influence can be exerted on which insect species can be brought to any locus or repelled from it.

In general, preferred mycopesticidal species as pathogens are somewhat slow-acting (that is, not immediately fatal) so as to avoid bait shyness and to avoid learning effects in social insects before individuals have distributed mycelium to all other members of the colony. To effect control of *Coptotermes formosanus* colonies, bait chemicals must kill slowly enough to allow foraging termites to return to the colony and spread the toxin to other colony members. Wright et al., Growth response of *Metarhizium anisopliae* to two Formosan subterranean termite nest volatiles, naphthalene and fenchone, *Mycologia,* 92(1): pp. 42-45 (2000) and the references therein. Bait shyness and other colony defense mechanisms such as segregation or avoidance of infected nestmates or necrophoretic behavior by the workers (i.e., removal of dead nestmates) serve as a means of defense against the spread of such pathogens when the targeted insect dies too quickly. For example, in general, queen fire ants will not feed on new foodstuffs until the food is first sampled by foragers or workers or members of expendable classes and deemed safe after a two or three day waiting period. Note, however, this general pattern may not always apply to the highly attractive mycoattractants and mycoattractants disclosed herein. Preconidial mycelium strains may be selected for virulence after an appropriate time period. In many applications it may be preferable to utilize a mixture or matrix of several species or strains of entomopathogenic fungus with different characteristics, maturation and growth rates including strains with delayed sporulation (and thereby prolonged attractant value) while in other applications a single species may be preferred. Similarly, with reference to a single species, a mixture of strains or a single strain may be utilized. A mixture of species and/or strains both allows the targeted insects to choose the species to which they are most attracted and provides for the possibility of simultaneous infection and insect plagues from multiple virulent species and strains.

Those skilled in the art will recognize that numerous entomogenous and entomopathogenic fungal species are known to the art and the above preconidial mycoattractant and mycopesticidal methods and products may be favorably applied to many or all such species, and it is the intent of the inventor that the invention be understood to cover such. Suitable entomopathogenic fungi include the Deuteromycetes *Metarhizium, Beauveria, Paecilomyces, Hirsutella, Verticillium, Culicinomyces, Nomuraea, Aspergillus* and other fungi imperfecti, sexually reproducing fungi such as the Ascomycetes *Cordyceps, Ascosphaera, Torrubiella, Hypocrella* and its *Aschersonia* anamorph, and the Pyrenomycete *Laboulbenia hageni*, the Basidiomycetes such as *Laccaria*, and combinations thereof. The Entomophthoracae including *Entomophaga, Massospora, Neozygites, Zoophthora, Pandora* and other Phycomycetes are also considered to be within the scope of the invention. Also included are such entomopathogenic species that have been genetically modified to be more virulent (including those modified via mutagenesis, hybridization and recombinant DNA techniques).

By way of example, but not of limitation, mycopesticidal species include *Metarhizium anisopliae* ("green muscarine"), *Metarhizium flaviride*, *Beauveria bassiana* ("white muscarine"), *Beauveria brongniartii*, *Paecilomyces farinosus*, *Paecilomyces fumosoroseus*, *Verticillium lecanii*, *Hirsutella citriformis*, *Hirsutella thompsoni, Aschersonia aleyrodis, Entomophaga grylli, Entomophaga maimaiga, Entomophaga muscae, Entomophaga praxibulli, Entomophthora plutellae, Zoophthora radicans, Neozygites floridana, Nomuraea rileyi, Pandora neoaphidis, Tolypocladium cylindrosporum, Culicinomyces clavosporus* and *Lagenidium giganteum*, the wide variety of *Cordyceps* and its imperfect forms including *Cordyceps variabilis, Cordyceps facis, Cordyceps subsessilis, Cordyceps myrmecophila, Cordyceps sphecocephala, Cordyceps entomorrhiza, Cordyceps gracilis, Cordyceps militaris, Cordyceps washingtonensis, Cordyceps melolanthae, Cordyceps ravenelii, Cordyceps unilateralis, Cordyceps sinensis* and *Cordyceps clavulata*, and mycorrhizal species such as *Laccaria bicolor*. Other mycopesticidal species will be apparent to those skilled in the art.

The concepts of "preconidial" and "spores" or "conidia" are complex, containing a number of different forms and specialized structures for reproduction of the fungi. Many fungi are pleomorphic, that is, one fungus may produce several sorts of spores which may or may not be coincident in time. With regard to the sexually reproducing *Cordyceps, Laccaria* and other "fungi perfecti," preconidial or pre-sporulation refers to the pre-fruiting state. The term "preconidial" or "pre-sporulation" has a somewhat different meaning with regard to the sexually reproducing fungi than with most other entomopathogenic fungi, as sexually reproducing fungi are "fungi perfecti" or mushroom fungi, whereas the non-mushroom fungi such as *Beauveria* and *Metarhizium* are the more primitive "fungi imperfecti." The situation is complicated by the fact that entomophthoralean fungi have complex life cycles involving non-sexual conidia and sexual resting spores. The situation is further complicated by the fact that some or all *Cordyceps* fungi are dimorphic and have a teleomorph (the sexual perfect form or morph, e.g. that characterized by sexual spores including acospores and basidiospores) and one or more anamorphs (the asexual imperfect form or morph, e.g. characterized by the presence or absence of conidia) with conidial stages within the imperfect fungal genera including *Beauveria, Metarhizium, Paecilomyces, Hirsutella, Verticillium, Aspergillus, Akanthomyces, Desmidiospora, Hymenostilbe, Mariannaea, Nomuraea, Paraisaria, Tolypocladium, Spicaria* (=*Isaria*) and *Botrytis*. For example, *C. subsessillis* is the perfect form of *Tolypocladium inflatum*, an anamorph (imperfect) form which produces cyclosporin. Hodge et al., *Mycologia* 88(5): 715-719 (1996). *Cordyceps militaris* (Fr.) Lk. is also thought to be dimorphic, the conidial stage of which is believed to be a *Cephalosporium. Cordyceps unilateralis* seems specific on the Camponotinii, while *Hirsutella sporodochialis* is probably an anamorph of *C. unilateralis* specific on *Polyrhachis*. Schmid-Hempel, supra, p. 43. DNA studies are expected to better elucidate these relationships. As used herein, unless otherwise specified, preconidial or pre-sporulation mycelium of sexually reproducing fungi refers to the pre-sporulation mycelial stage of the mushrooms, including any preconidial imperfect stages, but not any conidia bearing imperfect stages.

The "truly" social insects, or "eusocial" insects, include all of the ants, all of the termites and the more highly organized bees and wasps. These insects can be distinguished as a group by their common possession of three traits: (1) individuals of the same species cooperate in caring for the young; (2) there is a reproductive division of labor, with more or less sterile individuals working on behalf of fecund nestmates; and (3) there is an overlap of at least two generations in life stages capable of contributing to colony labor, so that offspring assist parents during some period of their life. Social pest insects are a particularly apt target for mycelial hyphae based control agents, as the mycelium may contact numerous individuals of varying castes and may infest housing structures. For example, *Metarhizium anisopliae* seems to attack only queens of *Solenopsis* in South America ("queen's disease); however, this may only look like a queen pathogen because infected workers leave the nest and are never found. Schmid-Hempel, supra, p. 110. Based upon observations to date and what is known to those skilled in the sciences concerned with entomology and entomopathogenic fungi, it is expected that preconidial mycoattractant and mycopesticidal products and methods may be similarly developed and applied favorably to all pest insects, including both social and non-social insects, and it is the intent of the inventor that the invention be understood to cover such.

Such mycoattractant and mycopesticidal preconidial fungi and extracts thereof are individually and/or collectively useful against such insects (Insecta) as termites (Isoptera) including Rhinotermitidae, Kalotermitidae, Termitidae, Mastotermitidae, Hodotermitidae and Serritermitidae such as subterranean termites, drywood termites, harvester termites, dampwood termites, desert termites and rottenwood termites, etc., including *Coptotermes formosanus* Shiraki (Formosan termite), *Reticulitermes* (e.g., *R. flavipes, R. virginicus, R. speratus, R. hesperus, R. tibialis, R. lucifugus, R. santonensis*), *Cryptotermes* (e.g. *C. domesticus* and *C. cubioceps*), *Acanthotermes, Ahamitermes, Allodontermes, Amitermes, Amitermitinae, Anacanthotermes, Archotermopsis, Armitermes, Calcaritermes, Capritermes, Cornitermes, Cubitermes, Drepanotermes, Globitermes, Glyptotermes, Heterotermes, Hodotermes, Hodotermopsis, Incisitermes* (e.g. *I. minor*), *Kalotermes* (e.g., *K. flavicollis*), *Labiotermes, Macrotermes, Macrotermitinae, Marginitermes, Mastotermes* (*M. darwiniensis*), *Microcerotermes, Microhodotermes, Nasutitermes, Nasutitermitinae, Neotermes, Odontotermes, Ophiotermes, Paraneotermes, Parastylotermes, Parrhinotermes, Pericapritermes, Porotermes, Prorhinotermes, Psammotermes, Rhinotermes, Rhynchotermes, Rugitermes, Schedorhinotermes, Serritermes, Stolotermes, Syntermes, Termes, Termitinae, Termitogeton, Termopsis* and *Zootermopsis*, and ants, wasps and bees (Hymenoptera) including, for example, ants (Formicoidea: Formicidae) such as the carpenter ants (Camponotini) *Camponotus modoc, C. vicinus, C. ferrugineus, C. floridanus, C. pennsylvanicus, C. herculeanus, C. varigatus, C. abdominalis* and *C. noveboracensis, Calomyrmex, Opisthopsis* and *Polyrhachis*, fire ants *Solenopsis invicta* and *S. richteri*, pharaoh ants (*Monomorium pharonis*), Argentine ants, pavement ants, odorous house ants and leaf cutter ants (*Atta* and *Acromyrmex*), wasps (Sphecoidea and Vespoidea) and bees (Apoidea including the Apidae "killer bees" *Apis mellifera adansonii* and *Apis mellifera scutellata* and hybrids thereof, particularly those hybrids with the European honey bee).

Just as the social insects have complex relationships with fungi in the wild, wood-boring beetles have intimate relationships with "ambrosia fungi" and other fungi as preferred food sources. It is expected that the preconidial mycopesticidal products and methods disclosed herein will be similarly useful as mycoattractants and/or mycopesticides with such beetles. By way of example but not of limitation, such beetles include bark, sap and wood-boring beetles such as the mountain pine beetle (*Dendroctonus ponderosae*), spruce beetle (*Dendroctonus rufipennis*), red turpentine beetle (*Dendroctonus valens*), black turpentine beetle (*Dendroctonus terebrans*), southern pine beetle (*Dendroctonus frontalis*), Douglas fir beetle (*Dendroctonus pseudotsugae*), engraver and *Ips* beetles including *Ips avulsus, Ips grandicollis, Ips calligraphus, Ips pini, Ips avulses*, and other sap beetles in the family Nitidulidae, powderpost beetles (Lyctidae), false powderpost beetles (Bostrichidae), deathwatch beetles, oldhouse borers, Asian long-horned beetle, etc.

It is further expected that the preconidial products and methods may, with no more than routine experimentation, prove useful against presocial, parasocial and subsocial insects including semisocial, quasisocial, communal and solitary insect pests such as cockroaches including American, German, Surinam, brown-banded, smokybrown, and Asian cockroaches, grasshoppers and locusts, crickets including mole cricket, Mormon crickets (actually a long-horned grasshopper), beetles, beetle grubs and beetle larvae including Colorado potato beetle (*Leptinotarsa decemlineata*) and other potato beetles, Mexican bean beetle, Japanese beetle, cereal leaf beetle, darkling beetle (lesser mealworm), Gypsy moths (*Lymantria dispar*) and Gypsy moth larvae, diamondback moths (*Plutella xylostella*), codling moth (*Laspeyresia pomonella*), Douglas fir tussock moth (*Orgyia pseudotsugata*), western spruce budworm (*Choristoneura occidentalis*), grape berry moths (*Lobesia lobina*), flies and fly larvae, springtails, large centipedes, shield centipedes, millipedes, European corn borers (*Ostrinia nubilalis*), Asiatic corn borers, velvetbean caterpillar (*Anticarsia gemmatalis*), other caterpillars and larvae of the Lepidoptera, whiteflies (*Dialeurodes* and *Bemisia* spp.), thrips (*Thrips* spp.), melon thrips (*Thrips palmi*), western flower thrips (*Frankliniella occidentalis*), aphids including Russian wheat aphid, spider mites (*Tetranychus* spp.), mealybugs including citrus mealybug (*Planococcus citri*) and *solanum* mealybug (*Pseudococcus solani*), boll weevils, black vine weevils (*Otiorhynchus sulcatus*), European pecan weevils (*Curculio caryae*), mosquitoes, wasps, sweet potato whiteflies, silverleaf whiteflies, cotton fleahoppers, pasture scarabs such as *Adoryphorus couloni* and other Scarabaeidae, spittle bug (*Mahanarva posticata*), corn earworm (*Helicoverpa zea*), American bollworm (*Heliothis armigera*), armyworms (*Pseudaletia unipuncta*), fall armyworm (*Spodoptera frugiperda*), southern armyworm (*Spodoptera eridania*), beet armyworm (*Spodoptera exigua*), yellowstriped armyworm (*Spodoptera ornithogalli*), black cutworm (*Agrotis ipsilon*), tobacco hornworm (*Manduco Sexta*), tobacco budworm (*Helicoverpa* (syn. *Helicoverpa*) *virescens*), sugar cane froghopper, rice brown planthopper, earwigs, loopers including cabbage looper (*Trichoplusia ni*), soybean looper (*Pseudoplusia includens*), forage looper (*Caenurgina erechtea*) and celery looper (*Anagrapha falcifera*), cabbageworms including the imported cabbageworm (*Pieris rapae*) and the European cabbageworm (*Pieries brassicae*), tomato pinworm (*Keiferia lycopersicella*), tomato hornworm (*Manduca quinquemaculata*), leafminers (*Liriomyza* spp.), cotton leafworm (*Alabama argillacea*), corn rootworm, garden webworm (*Achyra rantalis*), grape leaffolder (*Desmia funeralis*), melonworm (*Diaphania hyalinata*), pickleworm (*Diaphania nitidalis*), achemon sphinx (*Eumorpha achemon*), sweetpotato hornworm (*Agrius cingulata*), whitelined sphinx (*Hyles lineata*), lygus bugs (*Lygus* spp.), chinch bugs including *Blissus leucopterus* and false chinch bugs, sow bugs, pill bugs, citrus rust mite, pill wood lice, wheat cockchafer, white grubs and cockchafers, *Hoplochelis marginalis* and *Melolontha melontha*, storage pests such as *Prostephanus truncatus* and *Sitophilus zeamais*, soil insects, and various other insect pests in the orders, Isopoda, Diplopoda, Chilopoda, Symphyla, Thysanura, Collembola, Orthoptera, Dermaptera, Anoplura, Mallophaga, Thysanoptera, Heteroptera, Homoptera, Lepidoptera, Coleoptera, Diptera, Siphonaptera, Thysaoptera, Acarina, Arachnida, etc. and the families Plutellidae, Acrididae, Tettigoniidae, Gryllidae, Cryllotalpidae, Pyralidae, Sphingidae, Noctuidae, Pyralidae, Xylophagidae, Scarabaeidae, Scolytidae, Platypodidae, Lymexylidae, Nitidulidae, Pseudococcidae, Aphidae, Dalphacidae, Cicadellidae, Cercopidae, Aleyodidae, Coccoidea, etc. It will be recognized that the insects listed above are representative examples of insects which may be attracted and/or controlled according to the present invention, but such listing is not intended as a limitation to certain species as numerous other insect species to which the invention may be applied will be apparent to those skilled in the art.

It will be noted from the discussion above and examples and results below that attractiveness, pathogenicity and virulency toward the targeted insect are dependent in some degree upon factors including choice of mycopesticidal species, host range and specificity, selection of a strain within that species and selection of substrate. Entomopathogenic fungi also vary greatly in host specificity. Some entomopathogenic fungi are highly specific, such as *Pandora neoaphidis*, which is restricted to aphids. Other entomopathogenic fungi have wide host ranges, such as *Beauveria bassiana*, which is known to infect over 700 species of arthropods. Other species with wide host ranges include *Metarhizium anisopliae, Paecilomyces farinosus* and *Zoophthora radicans*. However, in the laboratory, isolates of fungi with wide host ranges are generally most virulent to the host from which they were first isolated; certainly their host range is much more restricted than that of the species to which they belong. Goettel et al., Safety to Nontarget Invertebrates of Fungal Biocontrol Agents, in: Laird et. al. (eds.) *Safety of Microbial Insecticides*, pp 209-232 (1990). Furthermore, fungi with wide host ranges are frequently even more specific under field conditions. There are reports of fungi attacking only one host even though closely related host species are present. Discrepancies between reports of social insect host specificity may be related to a general difference between tropical vs. temperate habitats rather than to the specific fungi and social insect species involved. Schmid-Hempel, supra at p. 44. Such specificity is thought to be due to the complex biotic and abiotic interactions in the field. This indicates that it should be possible, using no more than routine experimentation and bioassays of mycopesticidal strains and of the appropriate orders, families, genera, species and varieties of targeted pest insects, to isolate and use strains and substrates wherein the desired characteristics are maximized with respect to either a targeted insect or targeted insect group, thereby producing a species-specific, genus-specific, family-specific or order-specific entomopathogenic host specific fungal strain. Such entomopathogenic strains selected for host range and specificity may be similarly selected for minimal or no infection of or virulence towards beneficial insects or non-targeted insects.

For initial experimentation, a *Metarhizium anisopliae* from naturally occurring sources and the carpenter ant were selected. *M. anisopliae* was obtained from a public culture collection and used without further selection for virulence and/or pathogenicity; a publicly available strain free of proprietary or patent restrictions on use was selected as offering a preferred source and a more demanding initial test than strains selected for specific virulence. It will be understood, of course, that strains selected for specific characteristics of attractiveness to and/or virulence against specific insects will in general offer the best mode of practicing the invention. Cultures may be obtained from collections, isolated from the wild and/or reisolated from insects. The carpenter ant was selected for initial experimentation as offering several advantages: ants are typically more resistant to spores than termites and other insects, carpenter ants are a very destructive pest, the effect on other ant species could also be viewed, and the applicant enjoyed easy access to an experimental site as his residence was in danger of collapse due to long term structural infestation by carpenter ants and fungi.

EXAMPLE 1

*Metarhizium anisopliae* ATCC #62176 was grown in pure culture using standard fermentation techniques and diluted and aseptically transferred to grain (brown rice) which had been pressure steam-sterilized at one (1) kg/cm$^2$ (15 psi). The mycelium overgrew the rice and approximately 10-20 grams of preconidial mycelium of *Metarhizium anisopliae* was offered at the site of debris piles caused by carpenter ants (*Camponotus modoc*) at the interior face of an exterior wall of a wood frame residence located in Shelton, Wash., U.S.A. The mycelium was presented on a small dish and left exposed to the air. An observation made after three hours disclosed the carpenter ants feasting en masse on the non-sporulating, preconidial mycelium of the *Metarhizium* and approximately one dozen (12) carpenter ants were observed retreating into the wall, carrying pieces of the infectious mycelium with them. In a week's time, the carpenter ant colony became inactive and no evidence of carpenter ant activity was observed henceforth, saving the structure from further structural damage. Months later, the ecological niche once occupied by the carpenter ants was taken over by common household Sugar and Honey ants which were unaffected by the *Metarhizium anisopliae*. Carpenter ants have not been observed in the residence in the subsequent two years even though they are plentiful in a woodpile outside the house.

EXAMPLE 2

For "choice" tests, termite colony fragments of 50 pseudergates (workers) of the Eastern Subterranean Termite *Reticulitermes flavipes* (Kollar) or Formosan Subterranean Termite *Coptotermes formosanus* (Shiraki) [Isoptera: Rhinotermitidae] per test unit arena were collected prior to the start of the bioassay evaluation. The termite colony fragments were placed in plastic boxes with soil, adjusted to laboratory conditions and fed standard diet (standard tongue depressor section) and provided with a moistened cellulose source placed on top of the fungal preconidial mycelium in hexagonal weigh boats, perforated with 5 mm holes on all sides to allow termite entry. For "no-choice" or tube tests, termite colony fragments of 50 pseudergates (workers) per tube were collected prior to the start of the bioassay evaluation. Glass tubes were prepared containing fungal preconidial mycelium in the center, with moistened soil on each end of the mycelium, then bounded on each end by agar plugs. The bottom of the tube contained a 3 cm section of applicator stick, and was capped with foil and rubber banded. Termite colony fragments of 50 pseudergates were placed in the top section, above the agar plug, the end was capped with foil and rubber banded and observations were made as they tunneled down through the agar plug, top layer of soil, mycelium/rice mixture, and bottom layer of soil. Treatment was with preconidial mycelium products consisting of *Metarhizium anisopliae* ATCC #62176 on rice, *Beauveria bassiana* ATCC #20872 on rice and *Beauveria bassiana* ATCC #74038 on rice. There were four replicates of each of the test arenas and tubes for each termite species, and four replicates of control arenas, for a total of 16 arenas. Mortality (%) observations were recorded for both arena and tube bioassays.

*Metarhizium anisopliae* #62176 on rice was tunneled freely by both *Reticulitermes* and *Coptotermes* spp. in the test arenas. No significant mortality for either species was observed in the control or treatment arenas through day 28 of the evaluation.

*Beauveria bassiana* #20872 on rice was tunneled freely by both *Reticulitermes* and *Coptotermes* spp. with significant mortality in both *Reticulitermes* and *Coptotermes*. In the arenas, both species of termites built shelter tubes or soil connectives to the wood in the control samples and to the preconidial mycelium/rice product in the treatment samples. In the arena bioassay, significant mortality was observed in *Reticulitermes*, with a mean value of 52.5% for *Beauveria* #20872 on rice vs. a mean value of 1.25% for controls. In the arena bioassay with *Coptotermes*, significant mortality was observed for *Beauveria* #20872 on rice, with a mean value of 100% for treatments vs. a mean value of 2.5% for the controls.

In the tube bioassay, significant mortality was observed in *Reticulitermes*, with a mean mortality value of 65.5% for treatment with *Beauveria* #20872 on rice vs. a mean value of 1.67% for the controls. In *Coptotermes*, with *Beauveria* #20872 on rice, a mean value of 100% for the treatments vs. a mean value of 9.17% for the controls was obtained. Both species of termites tunneled through the control soil samples and agar sections. In the treatment samples, both species of termites tunneled through the top agar section and upper soil layer into the mycelium/rice product treatment area. *Reticulitermes flavipes* continued through the treatment and lower soil and agar section and placed soil around the wooden stick at the bottom, which is typical behavior of subterranean termites in a tube bioassay. *Coptotermes formosanus* termites, on the other hand, never left the mycelium/rice product treatment area. Atypically, they did not continue to tunnel through the lower soil and agar section to reach the wooden stick at the bottom of the tube. They were observed to remain in the preconidial mycelium test product, and at the end of the two week period, mortality levels were recorded at 100%.

With *Reticulitermes* utilizing *Beauveria bassiana* #20872 preconidial mycelium on wooden blocks, termites foraged to the blocks immediately. Within five days mortality began to be observed in the arenas with preconidial mycelium and mean mortalities of 90% and 100% were observed over 14 days.

EXAMPLE 3

Test unit colony fragments of 30 pseudergate *Reticulitermes flavipes* (Kollar) Eastern subterranean termites per tube bioassay were established as above and broken down after 14 days testing. There were three replicates of each of three test preconidial mycelium test strains and three control tubes, for a total of 12 tubes.

*Beauveria bassiana* #74038 on rice was freely tunneled in test arenas by the termites. Significant mortality (100%) was observed. A mortality of 45.56% was observed in controls.

*Beauveria bassiana* #20872 on rice was freely tunneled in test arenas by the termites. Non-significant mortality levels of 84.4% were observed with control group mortality of 45.56%.

*Metarhizium anisopliae* #62176 on rice was freely tunneled in test arenas by the termites. Non-significant mortality levels of 66.3% were observed with control group mortality of 45.56%.

| Eastern Subterranean Termite | % Mortality at 14 Days (3 replicates) |
|---|---|
| Strain # 74038 | 100 |
|  | 100 |
|  | 100 |
| Strain # 20872 | 53.3 |
|  | 100 |
|  | 100 |
| Strain # 62176 | 76.67 |
|  | 30.00 |
|  | 92.34 |
| Control | 56.67 |
|  | 23.34 |
|  | 56.67 |

EXAMPLE 4

Colony fragments of 100 *Solenopsis invicta* (Buren) red imported fire ants per standard plastic box test arena were established with moistened soil and preconidial mycelium. Three drops of water were added to the soil daily to maintain a humid medium amenable to ant activity and fugal growth. *Beauveria bassiana* #20872 and #74038 and *Metarhizium anisopliae* #62176 preconidial mycelium on rice were utilized as test strains. There were three replicates of each of three test strains and three control arenas, for a total of 12 arenas. In all test arenas portions of the preconidial mycelium were removed readily from the feeding dishes by the ants and scattered over the arena floors. Ants also readily moved into and created gallery-like tunnels in the preconidial mycelium on rice in the feeding dishes.

When considering the mortality numbers for all three strains, there was not a statistically significant difference from the control group at 7 days or 14 days post-association. This was also true at 21 days for #20872 and #62176.

| Red Imported Fire Ants | % Mortality (Mean value of 3 replicates) | | |
|---|---|---|---|
|  | 7 Days | 14 Days | 21 Days |
| Strain # 74038 | 39.33 | 80.33 | 98.00 |
| Strain # 20872 | 35.66 | 76.66 | 88.66 |
| Strain # 62176 | 39.66 | 62.66 | 82.33 |
| Control | 31.00 | 44.66 | 66.33 |

| Red Imported Fire Ants | % Mortality (3 replicates) | | |
|---|---|---|---|
|  | 7 Days | 14 Days | 21 Days |
| Strain # 74038 | 38 | 76 | 98 |
|  | 32 | 80 | 100 |
|  | 48 | 85 | 96 |
| Strain # 20872 | 39 | 83 | 94 |
|  | 42 | 84 | 100 |
|  | 26 | 63 | 72 |
| Strain # 62176 | 29 | 38 | 55 |
|  | 57 | 94 | 96 |
|  | 33 | 56 | 96 |
| Control | 54 | 71 | 82 |
|  | 14 | 24 | 46 |
|  | 25 | 39 | 71 |

EXAMPLE 5

Cultivate strains of *Metarhizium*, *Beauveria* and *Cordyceps* on grain, wood, or other cellulosic substrate as above under elevated $CO_2$ conditions to produce preconidial mycelium. Apply as attractant and/or pathogen at locations infested by insects such as carpenter ants, termites, beetles, flies, fire ants, cockroaches, grasshoppers, locusts and other insect pests and vermin.

EXAMPLE 6

In separate glass containers, extracts of *Beauveria bassiana* strains ATCC #20872 and ATCC #74038 were created from fresh preconidial mycelia grown out on organic short grain brown rice in spawn bags incubated for 11 days in class 100 clean room using the following procedures.

2,140 gm. (4.70 lb.) of ATCC #20872 *Beauveria bassiana* mycelium on rice was combined with 2,100 ml. (3.55 lb.) 95% (190 proof) organic grain alcohol diluted with 1,100 ml. (2.25 lb.) of spring water and macerated and incubated for a total of 14 days. Alcohol measured 45% at 14 days. An unusual characteristic, fragrance signature reminiscent of vanilla and Pepsi® cola was noted.

2,120 gm. (4.65 lb.) of ATCC #74038 *Beauveria bassiana* mycelium on rice was combined with 2,050 ml. (3.40 lb.) 95% (190 proof) organic gain alcohol diluted with 1,025 ml. (2.10 lb.) of spring water and macerated and incubated for a total of 14 days. Alcohol measured 50% at 14 days. A characteristic fragrance signature of old-fashioned hard Christmas candy was noted.

EXAMPLE 7

Alcohol extract of ATCC #74038 from Example 6 above was applied to wood which was placed in a test arena with Formosan termites, *Coptotermes formosanus*. Termites were observed streaming toward the bait. They continued to struggle to reach the bait as they were overcome by the alcohol fumes prior to death.

EXAMPLE 8

1) Extract fresh preconidial mycelium of an entomopathogenic fungi, for example *Beauveria, Metarhizium* or *Cordyceps* grown on grain, wood or paper, with 100% (anhydrous) or 95% (water/alcohol azeotrope) ethanol utilizing a Soxhlet or other extraction apparatus. Optionally remove the ethanol with a rotary evaporator or other apparatus prior to application and use.

2) Extract fresh entomopathogenic preconidial mycelium with a non-polar solvent, for example dichloromethane or toluene. Then extract the preconidial mycelium with a less polar solvent, for example acetone or isopropyl alcohol. Remove solvents under vacuum to obtain extracts.

3) Extract fresh preconidial mycelium on substrate with an organic solvent or mixture of solvents to obtain extracts.

Effect further purification if desired through chromatography, vacuum distillation and/or other purification methods. Isolate and characterize attractant fractions and compounds If desired. Synthesize attractant molecules, isomers and analogs if desired.

4) Place fresh preconidial entomopathogenic mycelium on grain in a flask and steam distill utilizing boiling water or introduced steam or superheated steam. Collect the condensate and separate steam-volatile attractant components from the aqueous phase utilizing separatory funnel or other apparatus. Extract aqueous phase with water-immiscible organic solvent or utilize "attractant water" as is.

No limitations with respect to the specific embodiments and examples disclosed herein are intended or should be inferred, as the examples and embodiments are representative only. While examples and preferred embodiments of the present invention have been shown and described, it will be apparent to those skilled in the art, or ascertainable using no more than routine experimentation, that many changes and modifications may be made without departing from the invention in its broader aspects. The appended claims are therefore intended to cover all such changes, modifications and equivalents as fall within the true spirit and scope of the invention.

I claim:

1. An entomopathogenic fungal composition comprising a preconidial mycelium of an entomopathogenic fungus cultivated on a solid substrate wherein the preconidial mycelium is cultured from a sector of an entomopathogenic fungus culture displaying the preconidial mycelium rather than those sectors displaying post-conidial mycelium and wherein the entomopathogenic fungus is selected from the group consisting of *Cordyceps* and *Cordyceps* anamorphs, *Metarhizium, Beauveria, Paecilomyces, Hirsutella, Verticillium, Culicinomyces, Nomuraea, Aspergillus, Ascosphaera, Hypocrella, Aschersonia, Torrubiella* and combinations thereof.

2. The entomopathogenic fungal composition of claim 1 wherein the entomopathogenic fungus is selected from the group consisting of *Metarhizium anisopliae, Metarhizium flaviride, Beauveria bassiana, Beauveria brongniartii, Paecilomyces farinosus, Paecilomyces fumosoroseus, Verticillium lecanii, Hirsutella citriformis, Hirsutella thompsoni, Aschersonia aleyrodis, Nomuraea rileyi, Tolypocladium cylindrosporum, Culicinomyces clavosporus, Cordyceps variabilis, Cordyceps facis, Cordyceps subsessilis, Cordyceps myrmecophila, Cordyceps sphecocephala, Cordyceps entomorrhiza, Cordyceps gracilis, Cordyceps militaris, Cordyceps washingtonensis, Cordyceps melolanthae, Cordyceps ravenelii, Cordyceps unilateralis, Cordyceps sinensis, Cordyceps clavulata* and combinations thereof.

3. The entomopathogenic fungal composition of claim 1 wherein the solid substrate is selected from the group consisting of grains, seeds, wood, paper products, cardboard, sawdust, corn cobs, cornstalks, chip board, hemp, jute, flax, sisal, reeds, grasses, bamboo, papyrus, coconut fibers, nut casings, seed hulls, straws, sugar cane bagasse, soybean roughage, coffee wastes, tea wastes, cactus wastes, banana fronds, palm leaves, fiberized rag stock, fabrics, landscaping cloths, geofabrics, soil blankets and rugs, mats, mattings, bags, baskets, gabions, fiber logs, fiber bricks, fiber ropes, nettings, felts, tatamis and combinations thereof.

4. The entomopathogenic fungal composition of claim 1 wherein the solid substrate is selected from the group consisting of cellulosic substrates, ligninic substrates, cellulolignic substrates, carbohydrate substrates and combinations thereof.

5. The entomopathogenic fungal composition of claim 1 wherein a strain of the entomopathogenic fungus is selected for pre-sporulation mycelium attractiveness to a targeted insect.

6. The entomopathogenic fungal composition of claim 1 wherein a strain of the entomopathogenic fungus is chosen for a characteristic selected from the group consisting of preconidial attractiveness to a targeted insect, phagostimulation, slowness to sporulate, mycelial pathogenicity and virulence, lack of virulence and pathogenicity, host specificity for targeted pest insects, time to insect death, mortality rate for pathogenic and virulent strains, low mortality rate of non-targeted insects, the proportion of kill of each life stage including larvae, pupae, workers, soldiers and royalty, high transmission rates, growth rate and speed of colonization of substrates, sensitivity and response to high and low carbon dioxide levels, recovery from metabolic arrest, recovery from transportation, stress tolerance, preferred temperature and humidity conditions, microflora sensitivity, ability to surpass competitors, adaptability to single component, formulated and complex substrates, high production of attractant extracts, genetic stability, non-sensitivity and resistance to chemical control agents, post-sporulation pathogenicity and combinations thereof.

7. The insect attractant and phagostimulant composition of claim 1 wherein the preconidial mycelium is metabolically arrested via a method selected from the group consisting of drying, freeze-drying, refrigerating, gaseous cooling, light deprivation, cryogenic suspension and combinations thereof.

8. An entomopathogenic fungal composition comprising a preconidial mycelium of an entomopathogenic fungus cultivated on a solid substrate wherein the preconidial mycelium is cultured from a sector of an entomopathogenic fungus culture displaying the preconidial mycelium rather than those sectors displaying post-conidial mycelium and wherein the entomopathogenic fungus is selected from the group consisting of *Metarhizium, Beauveria, Cordyceps*, anamorphs of *Cordyceps* and combinations thereof.

9. The entomopathogenic fungal composition of claim 8 wherein the entomopathogenic fungus is selected from the group consisting of *Metarhizium anisopliae, Metarhizium flaviride, Beauveria bassiana, Beauveria brongniartii, Cordyceps variabilis, Cordyceps facis, Cordyceps subsessilis, Cordyceps myrmecophila, Cordyceps sphecocephala, Cordyceps entomorrhiza, Cordyceps gracilis, Cordyceps militaris, Cordyceps washingtonensis, Cordyceps melolanthae, Cordyceps ravenelii, Cordyceps unilateralis, Cordyceps sinensis, Cordyceps clavulata* and combinations thereof.

10. The entomopathogenic fungal composition of claim 8 wherein the solid substrate is selected from the group consisting of grains, seeds, wood, paper products, cardboard, sawdust, corn cobs, cornstalks, chip board, hemp, jute, flax, sisal, reeds, grasses, bamboo, papyrus, coconut fibers, nut casings, seed hulls, straws, sugar cane bagasse, soybean roughage, coffee wastes, tea wastes, cactus wastes, banana fronds, palm leaves, fiberized rag stock, fabrics, landscaping cloths, geofabrics, soil blankets and rugs, mats, mattings, bags, baskets, gabions, fiber logs, fiber bricks, fiber ropes, nettings, felts, tatamis and combinations thereof.

11. The entomopathogenic fungal composition of claim 8 wherein the solid substrate is selected from the group consisting of cellulosic substrates, ligninic substrates, cellulolignic substrates, carbohydrate substrates and combinations thereof.

12. The entomopathogenic fungal composition of claim 8 wherein a strain of the entomopathogenic fungus is selected for pre-sporulation mycelium attractiveness to a targeted insect.

13. The entomopathogenic fungal composition of claim 8 wherein a strain of the entomopathogenic fungus is chosen for a characteristic selected from the group consisting of preconidial attractiveness to a targeted insect, phagostimulation, slowness to sporulate, mycelial pathogenicity and virulence, lack of virulence and pathogenicity, host specificity for targeted pest insects, time to insect death, mortality rate for pathogenic and virulent strains, low mortality rate of non-targeted insects, the proportion of kill of each life stage including larvae, pupae, workers, soldiers and royalty, high transmission rates, growth rate and speed of colonization of substrates, sensitivity and response to high and low carbon dioxide levels, recovery from metabolic arrest, recovery from transportation, stress tolerance, preferred temperature and humidity conditions, microflora sensitivity, ability to surpass competitors, adaptability to single component, formulated and complex substrates, high production of attractant extracts, genetic stability, non-sensitivity and resistance to chemical control agents, post-sporulation pathogenicity and combinations thereof.

14. The insect attractant and phagostimulant composition of claim 8 wherein the preconidial mycelium is metabolically arrested via a method selected from the group consisting of drying, freeze-drying, refrigerating, gaseous cooling, light deprivation, cryogenic suspension and combinations thereof.

15. An entomopathogenic fungal composition comprising an entomopathogenic fungus mycelium cultured on a solid substrate, wherein the entomopathogenic fungus mycelium is in a developmental state prior to spore formation, wherein the entomopathogenic fungus mycelium is cultured from a sector of an entomopathogenic fungus culture displaying pre-sporulation mycelium and wherein the entomopathogenic fungus is selected from the group consisting of *Metarhizium, Beauveria, Cordyceps* and combinations thereof.

16. The entomopathogenic fungal composition of claim 15 wherein the solid substrate is selected from the group consisting of grains, seeds, wood, paper products, cardboard, sawdust, corn cobs, cornstalks, chip board, hemp, jute, flax, sisal, reeds, grasses, bamboo, papyrus, coconut fibers, nut casings, seed hulls, straws, sugar cane bagasse, soybean roughage, coffee wastes, tea wastes, cactus wastes, banana fronds, palm leaves, fiberized rag stock, fabrics, landscaping cloths, geofabrics, soil blankets and rugs, mats, mattings, bags, baskets, gabions, fiber logs, fiber bricks, fiber ropes, nettings, felts, tatamis and combinations thereof.

17. The entomopathogenic fungal composition of claim 15 wherein the solid substrate is selected from the group consisting of cellulosic substrates, ligninic substrates, celluloligninic substrates, carbohydrate substrates and combinations thereof.

18. The entomopathogenic fungal composition of claim 15 wherein a strain of the entomopathogenic fungus is selected for pre-sporulation mycelium attractiveness to a targeted insect.

19. The entomopathogenic fungal composition of claim 15 wherein a strain of the entomopathogenic fungus is chosen for a characteristic selected from the group consisting of preconidial attractiveness to a targeted insect, phagostimulation, slowness to sporulate, mycelial pathogenicity and virulence, lack of virulence and pathogenicity, host specificity for targeted pest insects, time to insect death, mortality rate for pathogenic and virulent strains, low mortality rate of non-targeted insects, the proportion of kill of each life stage including larvae, pupae, workers, soldiers and royalty, high transmission rates, growth rate and speed of colonization of substrates, sensitivity and response to high and low carbon dioxide levels, recovery from metabolic arrest, recovery from transportation, stress tolerance, preferred temperature and humidity conditions, microflora sensitivity, ability to surpass competitors, adaptability to single component, formulated and complex substrates, high production of attractant extracts, genetic stability, non-sensitivity and resistance to chemical control agents, post-sporulation pathogenicity and combinations thereof.

20. The insect attractant and phagostimulant composition of claim 15 wherein the preconidial mycelium is metabolically arrested via a method selected from the group consisting of drying, freeze-drying, refrigerating, gaseous cooling, light deprivation, cryogenic suspension and combinations thereof.

* * * * *